United States Patent
Chowdhury et al.

(10) Patent No.: US 7,877,148 B2
(45) Date of Patent: Jan. 25, 2011

(54) EXTRAOCULAR DEVICE

(75) Inventors: Vivek Chowdhury, Randwick (AU); Minas Theodore Coroneo, Randwick (AU); John William Morley, Randwick (AU)

(73) Assignee: Sydney Biotech Pty. Ltd., Randwick (AU)

( * ) Notice: Subject to any disclaimer, the term of this patent is extended or adjusted under 35 U.S.C. 154(b) by 258 days.

(21) Appl. No.: 11/134,328

(22) Filed: May 23, 2005

(65) Prior Publication Data

US 2006/0095108 A1    May 4, 2006

(51) Int. Cl.
*A61N 1/20* (2006.01)
(52) U.S. Cl. .................... 607/54; 607/141
(58) Field of Classification Search .......... 607/54, 607/141
See application file for complete search history.

(56) References Cited

U.S. PATENT DOCUMENTS

| | | | | |
|---|---|---|---|---|
| 4,735,207 A * | 4/1988 | Nambu et al. | ............... | 600/476 |
| 4,753,655 A * | 6/1988 | Hecht | ............... | 128/898 |
| 5,024,223 A * | 6/1991 | Chow | ............... | 607/53 |
| 5,147,284 A * | 9/1992 | Fedorov et al. | ............... | 600/9 |
| 5,178,604 A * | 1/1993 | Baerveldt et al. | ............... | 604/8 |
| 5,556,423 A * | 9/1996 | Chow et al. | ............... | 623/6.63 |
| 5,935,155 A * | 8/1999 | Humayun et al. | ............... | 607/54 |
| 6,099,457 A * | 8/2000 | Good | ............... | 600/8 |
| 6,102,045 A * | 8/2000 | Nordquist et al. | ............... | 128/898 |
| 6,230,057 B1 * | 5/2001 | Chow et al. | ............... | 607/54 |
| 6,427,087 B1 * | 7/2002 | Chow et al. | ............... | 607/54 |
| 6,442,431 B1 | 8/2002 | Veraart et al. | | |
| 6,976,982 B2 * | 12/2005 | Santini et al. | ............... | 604/891.1 |
| 7,003,354 B2 * | 2/2006 | Chow et al. | ............... | 607/54 |
| 7,003,355 B1 * | 2/2006 | Suaning et al. | ............... | 607/54 |
| 7,020,527 B2 * | 3/2006 | Morimoto et al. | ............... | 607/50 |
| 7,035,692 B1 * | 4/2006 | Maghribi et al. | ............... | 607/53 |
| 2003/0139784 A1 * | 7/2003 | Morimoto et al. | ............... | 607/54 |
| 2004/0098067 A1 * | 5/2004 | Ohta et al. | ............... | 607/54 |
| 2004/0106965 A1 | 6/2004 | Chow | | |
| 2004/0180075 A1 * | 9/2004 | Robinson et al. | ............... | 424/428 |

(Continued)

FOREIGN PATENT DOCUMENTS

EP    1 386 636 A    2/2004

OTHER PUBLICATIONS

Sharma et al, *Survey of Ophthalmology*, 43(5):427-444 (1999).

(Continued)

*Primary Examiner*—Carl H Layno
*Assistant Examiner*—Paula J Stice
(74) *Attorney, Agent, or Firm*—Sughrue Mion, PLLC

(57) ABSTRACT

A medical device for use on the human eye is described. The device is placed in an extrocular location in a patient and delivers an electrical current that stimulates the retina of patients who are blind or have vision disorders. It has at least one electrode that makes contact with the scleral surface of the eye, the electrode typically being activated by an electrical stimulator. The device produces electrical pulses which pass through the electrodes on the scleral surface of the eye, to activate the retina of the eye, which causes the patient to experience improved vision, visual sensations or the prevention of deterioration of vision. By this means, sight can be restored or improved where patients have disorders of their retina or other parts of their visual system.

45 Claims, 23 Drawing Sheets

U.S. PATENT DOCUMENTS

| | | | |
|---|---|---|---|
| 2004/0186533 A1* | 9/2004 | Greenberg et al. | 607/54 |
| 2005/0004625 A1* | 1/2005 | Chow | 607/54 |
| 2005/0004626 A1* | 1/2005 | Terasawa et al. | 607/54 |
| 2005/0251223 A1* | 11/2005 | Eckmiller | 607/54 |
| 2006/0036295 A1* | 2/2006 | Greenberg et al. | 607/54 |
| 2006/0036296 A1* | 2/2006 | Greenberg et al. | 607/54 |
| 2006/0111757 A9* | 5/2006 | Greenberg et al. | 607/54 |

OTHER PUBLICATIONS

Chong et al, *Br. J. Ophthalmol*, 83:120-122 (1999).
Mitchell et al, Repair: Cell Regeneration, Fibrosis and Wound Healing, In: Kumar et al, eds., *Basic Pathology*, 6 ed., Philidelphia: Saunders, pp. 48-49 (1997).
Scarlatis et al, *JAMA*, 283(17):2297 (2005).
Larkin, *Lancet*, 355(9209):1080 2000.
Veraat et al, *Brain Research*, 813:181-186 (1998).
Maynard et al, *Annu. Rev. Biomed. Eng.*, 3:145-168 (2001).
Brindley et al, *J. Physiol.*, 196:479-493 (1968).
Humayun et al, *Archives of Ophthalmology*, 114(1):40-46 (1996).
Dobelle et al, *ASAIO Journal*, 46(1):3-9 (2000).
Grumet et al, *J. of Neuroscience Methods*, 101:31-42 (2000).
Humayun et al, *Vision Research*, 39:2569-2576 (1999).
Chow et al, *Neuroscience Letters*, 255:13-16 (1997).
Stett et al, *Vision Research*, 40:1785-1795 (2000).
Rizzo et al, *Ophthalmology*, 108(1):13-14 (2001).
Margalit et al, *Survey of Ophthalmology*, 47 (4) :335-356 (2002).
Chow et al, *Neuroscience Letters*, 225(1) :13-16 (1997).
Humayun et al, *Vision Research*, 43:2573-2581 (2003).
Dawson et al, *Invest Ophthalmol Vis. Sci.*, 16(3):249-252 (1977).
Yoemans, *Priniciples of Brain Stimulation*, New York: Oxford University Press (1990).
Eckmiller et al, *Ophthalmic Res.*, 29:281-289 (1997).
Jensen et al, *IOVS*, 44(8):3533-3543 (2003).
Walter et al, *Retina*, 19(6):546-552 (1999).
Majji et al, *Investigative Ophthalmology & Visual Science*, 40(9):2073-2081 (1999).
McCreery et al, *IEEE Transactions on Biomedical Engineering*, 37(10):996-1001 (1990).
Agnew et al, *Epilepsia*, 31(*Suppl. 2*):S27-S32 (1990).
Lamme et al, *Vision Research*, 40:1507-1521 (2000).
Gordon et al, *Electroencephalography & Clinical Neurophysiology*, 75(5):371-377 (1990).
Jayakar, *Advances in Nuerology*, 63:17-27 1993.
Tusa et al, *J. Comp. Neural*, 177(2):213-235 (1978).
Humayun, *Tr. Am. Ophth. Soc.*, 99:271-300 (2001).

* cited by examiner

LEGEND

M: Medical

L: Lateral

S: Superior

I: Inferior

SO: Superior Oblique Muscle Attachment

IO: Inferior Oblique Muscle Attachment

ORA: Ora Serrata

CAT A

CAT B

EXTRAOCULAR DEVICE

FIELD OF THE INVENTION

The present invention relates generally to devices for enhancing visual perception, and more particularly to devices that generate electrical impulses in an extraocular location of an eye of a patient, to deliver electrical stimuli to a retinal region in the eye of the patient for restoration or enhancement of visual perception, or prevention of deterioration to visual perception.

BACKGROUND OF THE INVENTION

Loss or impairment of visual perception can result from a variety of causes. Examples include diseases that cause deterioration of the retina, such as Retinitis Pigmentosa, which affects over one million people worldwide, and can lead to profound blindness. Other such diseases include Usher syndrome, age-related macular degeneration, Stargardt macular dystrophy, Leber congenital amaurosis and Bardet-Biedl syndrome.

There is currently no clinical means of restoring visual perception to patients who have developed blindness (no light perception) as a result of Retinitis Pigmentosa or other inherited or acquired retinal dystrophies. There is also no clinical means of preventing the deterioration towards blindness that occurs in the retinal dystrophies, (Sharma R K, & Ehinger B. Management of hereditary retinal degenerations: present status and future directions. *Survey of Ophthalmology* 1999; 43(5):427-44.; Chong N H, & Bird A C. Management of inherited outer retinal dystrophies: present and future. *British Journal of Ophthalmology* 1999; 83(1):120-2).

Experimental treatments such as gene therapy, neural cell transplantation, growth factors, vitamin supplementation, antioxidants and regulators of apoptosis have shown no success in restoring visual sensations to blind patients in clinical trials (Sharma & Ehinger, 1999, above). It is unlikely that any of these methods will be able to restore visual perceptions to blind patients in the medium term (5-10 years), if at all (Chong & Bird, 1999, above). This is due to the poor capacity of neural tissue, such as that in the retina, for repair and regeneration (Mitchell R N, & Cotran R S. Chapter 3: Repair: Cell Regeneration, Fibrosis, and Wound Healing. In: Kumar V, Cotran R S, Robbins S L, eds. Basic Pathology. 6 ed. Philadelphia: W. B. Saunders, 1997). Therefore an approach to restoring vision based on bypassing the damaged elements of the visual pathway is required (Scarlatis G. Optical prosthesis: visions of the future. *JAMA* 2000; 283(17):2297.; Larkin M. Artificial-vision research comes into focus. *Lancet* 2000; 355(9209):1080).

The only experimental method that has successfully restored visual perceptions to irreversibly blind patients is electrical stimulation of the eye, optic nerve or brain with implanted electrodes (Veraart et al. 1998, above; Maynard E M. Visual prostheses. *Annual Review of Biomedical Engineering* 2001; 3:145-68; Brindley G S, & Lewin W S. The sensations produced by electrical stimulation of the visual cortex. *Journal of Physiology* 1968; 196(2):479-93; Humayun et al. Visual perception elicited by electrical stimulation of retina in blind humans. *Archives of Ophthalmology* 1996; 114(1):40-6). Of these three approaches, electrical stimulation of the visual cortex is also the only approach to developing a bionic eye so far that has restored visual perceptions that are able to increase a blind patient's mobility and independence (Dobelle W H. Artificial vision for the blind by connecting a television camera to the visual cortex. *ASAIO Journal* 2000; 46(1):3-9).

Electrical currents can have many effects on the eye. One such effect is a therapeutic effect, whereby electrical current can help to heal cells and tissues that have been damaged by disease and therefore improve vision. Electrical current can also be used to activate surviving nervous cells in the eye that have lost their natural input due to a disease process. By activating these surviving cells, signals are relayed to brain which cause a patient to perceive a visual sensation, and such electrically evoked, artificially induced visual phenomena are called "phosphenes". This is generally known as a prosthetically induced visual effect.

The use of electricity in a therapeutic capacity to heal tissues in the eye has been suggested by a number of researchers: for example, in 1989, Shandurina and colleagues working at the Academy of Medical Sciences in Russia, reported successful results from therapeutic electrical stimulation of the optic nerve in patients with visual impairment. In 2003, Chow, et al. (Chow et al. Subretinal Artificial Silicon Retina Microchip Implantation in Retinitis Pigmentosa Patients: Long Term Follow-Up. *ARVO Meeting Abstracts* 2003; 44(5):4205) reported that electrical stimulation from a device that they had implanted intraocularly near the retina of patient's eyes was improving the subjects vision by having a neurotrophic effect on the diseased retinal tissues. U.S. Pat. No. 5,147,284, to Federov, describes a device consisting of two electrodes, one placed on the optic nerve and one placed on the sclera, for the treatment of visual disorders such as optic atrophy through electrical stimulation.

Other approaches to improve visual perception using electrical stimulation include placement of a device which has photosensitive components and electrodes at a "subretinal location" at the outer aspect of the neuroretina. Examples of such devices are described in U.S. Pat. No. 2,760,483 to Tassicker, U.S. Pat. No. 5,016,633 to Chow and U.S. Pat. No. 6,347,250, to Nisch.

Another approach is to place electrodes at an "epiretinal" location on the surface of the retina, between the retina and the vitreous. Such approaches are described in U.S. Pat. No. 5,109,844, to De Juan, and U.S. Pat. No. 6,324,429, to Shire.

Another approach is to implant electrodes to electrically stimulate the optic nerve. This is described, for example, in U.S. Pat. No. 6,442,431, to Veraart.

Devices have also been proposed for direct electrical stimulation of the visual region of the brain, by using electrical stimulation of the visual system to elicit phosphene perception. There have been a number of different approaches to the design of a device for this purpose, described for example in U.S. Pat. No. 5,215,088 to Normann, which discusses penetrating electrodes for implantation into the tissues of the brain.

It is surprising that despite an intensive research effort by a number of well-funded groups over the past 10 years aimed at developing a visual prosthesis with intraocular electrodes placed at an epiretinal, (Humayun et al. 1996 above; Grumet et al., Multi-electrode stimulation and recording in the isolated retina *Journal of Neuroscience Methods* 2000; 101(1): 31-42; Humayun M S. Intraocular retinal prosthesis. *Transactions of the American Ophthalmological Society* 2001; 99:271-300; de Juan et al. Pattern electrical stimulation of the human retina. *Vision Research* 1999; 39(15):2569-76,) or subretinal, (Chow A Y & Chow V Y. Subretinal electrical stimulation of the rabbit retina. *Neuroscience Letters* 1997; 225(1):13-6.; Stett et al., Electrical multisite stimulation of the isolated chicken retina. *Vision Research* 2000; 40(13):

1785-95) location, electrical stimulation of the retina has not met with the success of visual cortex stimulation (Rizzo et al. Retinal prosthesis: an encouraging first decade with major challenges ahead. *Ophthalmology* 2001; 108(1):13-4). This is because there are significant problems to be overcome at the electrode-tissue interface before an intraocular retina-based bionic implant can be considered a viable approach to treating blindness (Rizzo J F, Wyatt J, Humayun M, et al., above; Margalit, et al. Retinal prosthesis for the blind. *Survey of Ophthalmology* 2002; 47(4):335-56).

Currently there are two chronic trials of intraocular retinal implants occurring. In a study of subretinal stimulation by Chow et al, improvements in the visual acuity of implanted patients could not be explained by a neuroprosthetic effect of the implanted device, and the investigators have suggested that low level electrical stimulation of the retina is having a yet undefined "neurotrophic effect" (Chow et al. 2003, above). Regardless of whether this hypothesis is verified, these devices are not acting as conventional neural prostheses (Chapin J K & Moxon K A. Neural prostheses for restoration of sensory and motor function. Boca Raton: CRC Press, 2001), and are instead using electrical stimulation for a therapeutic effect.

In the other study by Humayun et el. (Humayun et al. Visual perception in a blind subject with a chronic microelectronic retinal prosthesis. *Vision Res* 2003; 43(24):2573-81.), a 4×4 array of 16 platinum disc electrodes, each of 520 µm diameter, with an inter-electrode centre-to-centre spacing of 720 µm was implanted with a tack at the epiretinal surface of a blind human patient. A cable from the electrode array passed through the sclera and tracked subcutaneously to a stimulator outside the orbit. Electrical stimulation of this array elicited the subjective perception of small spots of light in the patient's visual field. Interfacing the device with a camera allowed the patient to detect the presence of light and large objects (Humayun et el. 2003, above).

Hence, the devices and approaches of the prior art involve invasive stimulation of the visual system, and in particular, the eye and optic nerve, of patients suffering visual impairments. There thus remains a need for new approaches for enhancing or restoring visual perception in patients, or preventing deterioration of visual perception in patients, that do not require such invasive and potentially dangerous surgery.

SUMMARY OF THE INVENTION

The present inventors have found that perceptual results, attained with an epiretinal device, can be more effectively and safely obtained by using extraocular stimulation of the retina with an electrode array placed on the scleral surface of the eye. There are many benefits of such an approach as it does not require intraocular surgery, or the implantation of an intraocular foreign body. Furthermore, there is no requirement for a cable passing through the sclera, which leaves a permanent defect in the integrity of the globe.

Thus, in its broadest form, the present invention relates to an extraocular device comprising:
  at least one electrode; and
  a stimulator; and
  a conducting means for electrically connecting the one or more electrodes to the stimulator
  wherein the electrode is retained on an outer scleral surface of an eye of a subject, the stimulator providing an electrical impulse that travels through the conducting means to said one or more electrodes and the outer scleral surface of the eye, to stimulate retinal tissue in the eye.

Preferably, the one or more electrodes are embedded in a continuous base member housing said one or more electrodes and permitting intimate physical contact between said one or more electrodes and the outer scleral surface of the eye.

Even more preferably, the base member is retained on the scleral surface by sutures, a bioadhesive glue or the shape of the base member in relation to the scleral surface.

In another form, the one or more electrodes are embedded in separate bases, wherein each base is retained on the scleral surface by sutures or a bioadhesive glue.

In another form, the base member is shaped to conform to the external scleral surface of the eye of a subject, and preferably, the external scleral surface of the globe of the eye.

Even more preferably, the shape of the base member retains it on the scleral surface of the eye.

In one embodiment, the base member includes perforations to decrease the degree of separation of connective tissues overlying the sclera of the eye from the sclera of the eye.

In another preferred form, the base member is a strip shape comprising a linear array of electrodes.

Preferably, the base member is shaped to be placed on the scleral surface of the eye without disrupting attachment of the optic nerve and to fit around further anatomical structures of the eye, such as the attachment of one or more rectus muscles.

In one form, the base member completely surrounds the sclera of the eye.

In another form, the base member surrounds a portion of the sclera of the eye.

In a preferred form, a posterior portion of the base member has an elongate aperture allowing sliding placement of the base member about the optic nerve of the eye.

Preferably, the device has between 1 and 1000 electrodes.

Even more preferably, each electrode has an independent conducting means, each conducting means being insulated.

In one form of the device, the stimulator is implanted in the body of the subject, for example, inside the orbit of the subject.

In another form, the stimulator is located outside of the body, the conducting means exiting the body through a percutaneous connection to meet the stimulator.

Preferably, the stimulator is powered by a battery.

In another preferred form, the stimulator is powered and controlled by an inductive link from a transmission coil that has been placed outside the body.

Preferably, the base member comprises a biocompatible material such as a silicone elastomer.

Even more preferably, the conducting means is insulated with a biocompatible material.

Preferably, the biocompatible material covers a connection between the conducting means and the stimulator.

In a particularly preferred form, the stimulator is controlled by a preprogrammed sequence of electrical stimulation.

Preferably, the at least one electrode is platinium or a platinium alloy.

Even more preferably, the electrical impulse provided by the stimulator comprises a monopolar, bipolar or multi-polar electrical impulse.

Preferably, the stimulator provides an electrical impulse that is a constant-current pulse having a duration between 10 µs and 10 ms Even more preferably, the stimulator provides an electrical impulse having a current intensity between 1 µA and 10 mA.

In a further preferred form, the stimulator provides an electrical impulse that is a biphasic pulse or a monophasic pulse.

In yet another preferred form, the stimulator provides an electrical impulse having a frequency between 0.01 Hz and 250 Hz.

In another broad form, the present invention relates to an extraocular device comprising:

at least one electrode; and means for electrically stimulating the one or more electrodes wherein the one or more electrodes are retained on an outer scleral surface of an eye of a subject, with electrical stimulation of the one or more electrodes providing an electrical impulse in the one or more electrodes and the outer scleral surface of the eye, to stimulate retinal tissue in the eye.

Preferably, the means for electrically stimulating the electrodes is a laser light source.

In another form, the invention relates to a method of restoring, improving or preventing deterioration of visual perception in a patient having a visual disorder, the method comprising applying an extraocular electrical impulse to a scleral surface and of an eye and thereby to retinal cells of the eye of the patient.

In yet another form, the invention relates to a method for generating a phosphene in a patient having a visual disorder, the method comprising applying an extraocular electrical impulse to a scleral surface of an eye and thereby to retinal cells of the eye of the patient.

Preferably, the visual disorder is a retinal dystrophy selected from the group comprising retinitis pigmentosa, Usher syndrome, age-related macular degeneration, Stargardt macular dystrophy, Leber congenital amaurosis or Bardet-Biedl syndrome.

Preferably, the electrical impulse is delivered to the scleral surface using an extraocular device of the invention.

BRIEF DESCRIPTION OF THE DRAWINGS

Examples of the present invention will now be described with reference to the accompanying drawings, in which.

DETAILED DESCRIPTION OF THE INVENTION

Figure 1:
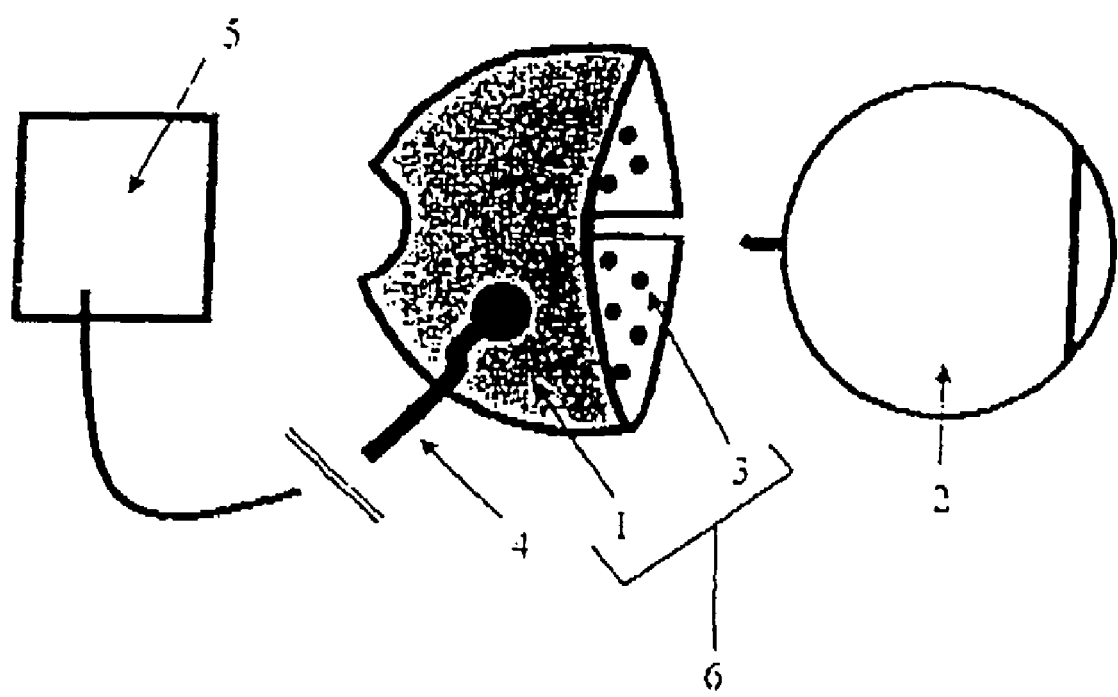
FIG. 1 is a schematic diagram of an example of an extraocular device of the invention.

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The present invention relates to a device to be used for providing electrical stimulation to the eye. The purpose of providing electrical stimulation is to deliver a therapeutic or neuroprosthetic effect to a diseased eye. A therapeutic effect is an electrical stimulation of the eye that aims in assisting the healing and regeneration of damaged tissue. This will then lead to an improvement in the vision of a patient with diseases of their eyes or other parts of their visual system, and thus prevent the patient's vision from deteriorating further. A neuroprosthetic effect is electrical stimulation of the eye with the aim of activating cells such as neurons in the eye which can relay signals to the visual centers of the brain. Electrical activation of such cells causes a patient to experience the visual phenomenon of a small spot of light in their visual field, called a "phosphene". By eliciting phosphene perception through electrical stimulation the device can restore or improve vision to patients who are blind or have lesser degrees of visual impairment, and thus also prevent further deterioration of vision in patients who have not lost all visual sensation. The aim of a visual prosthesis is to convey to the patient a rudimentary image of the surrounding environment built up of a number of phosphene "pixels". Visual prostheses are being developed that electrically stimulate the visual pathway at the level of the retina, the optic nerve and the visual cortex.

The present inventors have established the feasibility of an extraocular approach to retinal stimulation. This is the first study of an extraocular retinal prosthesis, an approach to visual prosthesis development for which a device has hitherto not yet been developed (Maynard E M. 2001, above), (Margalit et al., 2002 above), (Humayun M S, et al., 2003 above).

The present invention thus discloses devices for electrical stimulation of the eye via electrodes placed on the scleral surface of the eye. As such it is an extraocular device, which achieves electrical stimulation of the eye from electrodes placed in an extraocular location on the external surface of the sclera. Unlike devices of the prior art (eg. Fedorov U.S. Pat. No. 5,147,284), which discloses a device for electrical stimulation between an electrode on the optic nerve and an electrode on the scleral equator, the devices of the present invention do not have electrodes attached to the optic nerve.

The present invention has one or more scleral electrode. The present invention presents unique designs of devices for electrode implantation on the scleral surface of the eye from both therapeutic and visual prosthesis uses.

There are considerable advantages to using an extraocular (scleral) eye stimulator over epiretinal and subretinal visual prostheses previously disclosed. It does not require intraocular surgery, it does not require placing a chronic foreign body in the intraocular compartment and it does not require cables to be passed in and out of the eye through the sclera as in previously disclosed inventions. The device is much easier to implant and remove than intraocular devices. The device is also much easier to manufacture than intraocular devices. By having the tough yet thin sclera between the device and the retina; it protects the delicate tissues of the retina from direct mechanical trauma, and heat and charge effects from electrical stimulation with the device, as compared with intraocular epiretinal and subretinal implants.

In one form, the extraocular device consists of three components. These components are at least one electrode, a conducting means and a stimulator.

Preferably, the electrodes are housed in a continuous base (referred to herein as a base member), or each electrode is housed in its own base.

The conducting means connects the base member or bases to the stimulator. The base member or bases can have a variety of shapes depending on the embodiment of the invention, and there can be from approximately 1 to 1000 electrodes, or more, of varying size, shape and inter-electrode configuration depending on the embodiment.

The base member or bases of the device are implanted in the human body on the surface of the eye. After a surgical approach to gain access to the scleral surface of the eye, the device is placed on this surface. In one embodiment, the base member is shaped to conform to the curvature and shape of the external scleral surface of the globe of the eye. The base member is shaped to be placed on the scleral surface of the eye without disrupting the attachment of the optic nerve exiting from the posterior of the globe. The base member is shaped to fit around other structures that attach to the scleral surface of the globe, such as the attachment of the rectus muscles, depending on the objective of the embodiment. Examples of suitable attachment means whereby the base member conforms to the outer surface of the sclera include embedding one or more electrodes in a scleral buckle, which are devices that are commonly known in the field. Electrode-embedded scleral buckles can be placed on the scleral surface in the same manner as standard scleral buckles, when used for other eye conditions (eg. retinal detachment).

In an alternative form of the invention, the base member or individual bases of the device of the invention are retained on the scleral surface using a suitable, long-term, bioadhesive glue. Suitable examples are well known in the art and include cyanoacrylates (eg. N-butyl cyanoacrylates), and fibrin glue.

In one form, the device has a base member in which electrodes may be embedded. The electrodes have active surfaces which are directed towards the inner surface of the base member of the device, so that when the base member is applied to the scleral surface of the eye, the base member conforms to the shape of the globe, and the active surfaces of the electrodes come into contact with the scleral surface of the eye. In this embodiment, each electrode has an independent insulated conductor which travels in the substance of the base member and exits the base member at the point where the conducting means is attached to the base member.

In this form of the invention, the conducting means attaches to the outer surface of the base member and carries the individual insulated conductors from the electrodes. The conducting means connects the base with the stimulator, which may be implanted in the human body. Alternatively the conducting means may exit the body through a percutaneous connection and connect with a stimulator outside the body. In another form, the conducting means may attach to a percutaneous plug, to which an external stimulator can be interfaced.

In one embodiment, the stimulator is a device which is implanted in the body in a location that is outside the orbit or inside the orbit. The stimulator produces electrical pulses that are conducted through the conducting means of the stimulator to the electrodes on the bases or base member, which are applied to the outer scleral surface of the eye. The stimulator may be powered by battery and run a pre-programmed sequence of stimulation. Alternatively the stimulator may be powered and controlled by an inductive link from a transmission coil that has been placed outside the body.

In a further form, the function of the electrical stimulator is replaced with a means for electrically stimulating the one or more electrodes of the device. Suitable means for activating electrodes are well known in the art, and include, but are not limited to, laser light or conventional light sources.

The base member is suitably composed of a biocompatible material such as, but not limited to, a silicone elastomer. Such a suitable biocompatible material will also insulate the conducting means, and cover the conducting means to its connection with the stimulator. Preferably, the electrodes are composed of a material suitable for electrical stimulation such as, but not restricted to, platinum and its alloys.

Electrical stimulation of the eye may occur through monopolar, bipolar, and multi-polar electrical stimulation of the electrodes on the grid through a variety of different configurations. Stimulus parameters will include, but are not limited to, constant-current pulses, of pulse durations between 10 µs and 10 ms and current intensity levels between 1 µA and 10 mA. Biphasic or monophasic pulses may be used. Trains of stimuli with frequencies between 0.01 Hz and 250 Hz may be used.

In a particularly preferred embodiment, the present inventors seek to adapt the neuroprosthetic technology that is available in the Nucleus 24 Auditory Brainstem Implant (Cochlear Ltd, Australia). This implant has an electrode array of 21 platinum disc electrodes, each of 700 µm diameters, with a 950 µm centre-to-centre inter-electrode spacing, arranged in three rows in a silicone carrier.

The present inventors have investigated a number of electrode types, configurations, and stimulus methods to optimize the development of an extraocular retinal implant for the restoration of visual perception to blind patients.

An example of an extrocular device according to the invention will now be described with reference to FIG. 1, which illustrates an overview of the three components of the invention. The base member 6, forms the main body of the device and preferably consists of a biocompatible insulating material 1 such as a silicone elastomer, in which are embedded the electrodes 3, whose active surfaces on the inner aspect of the base member are applied to the scleral surface of the eye 2, after the base member is implanted over the eye.

According to this embodiment, extending from the lateral surface of the base member (when viewed after implantation on the eye), is the conducting means 4, which contains independent conductors from all the electrodes in the base. The conducting means 4, however, may exit from the base at any location that is feasible. In the present examples, the conducting means 4 connects the base with the stimulator 5.

Figure 2:
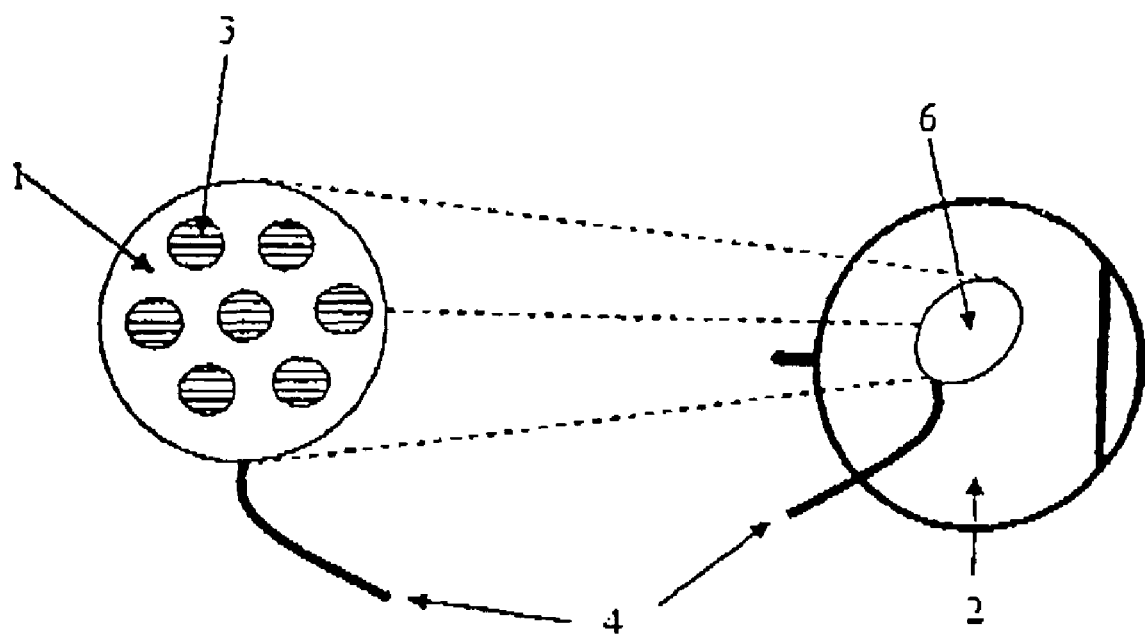
FIG. 2 is a plan view of the scleral-contacting surface of the base and its relation to the conducting means of an example of a device of the invention.

FIG. 2 illustrates a further example of an extraocular device of the invention. In this examples the base member 1 does not extend all around the sclera as in FIG. 1, but occupies a localised region 6 on the scleral surface. The scleral face of the base member is shown. In this embodiment the base 1 has a circular shape, and as in FIG. 1, contains multiple embedded electrodes 3.

Figure 3:
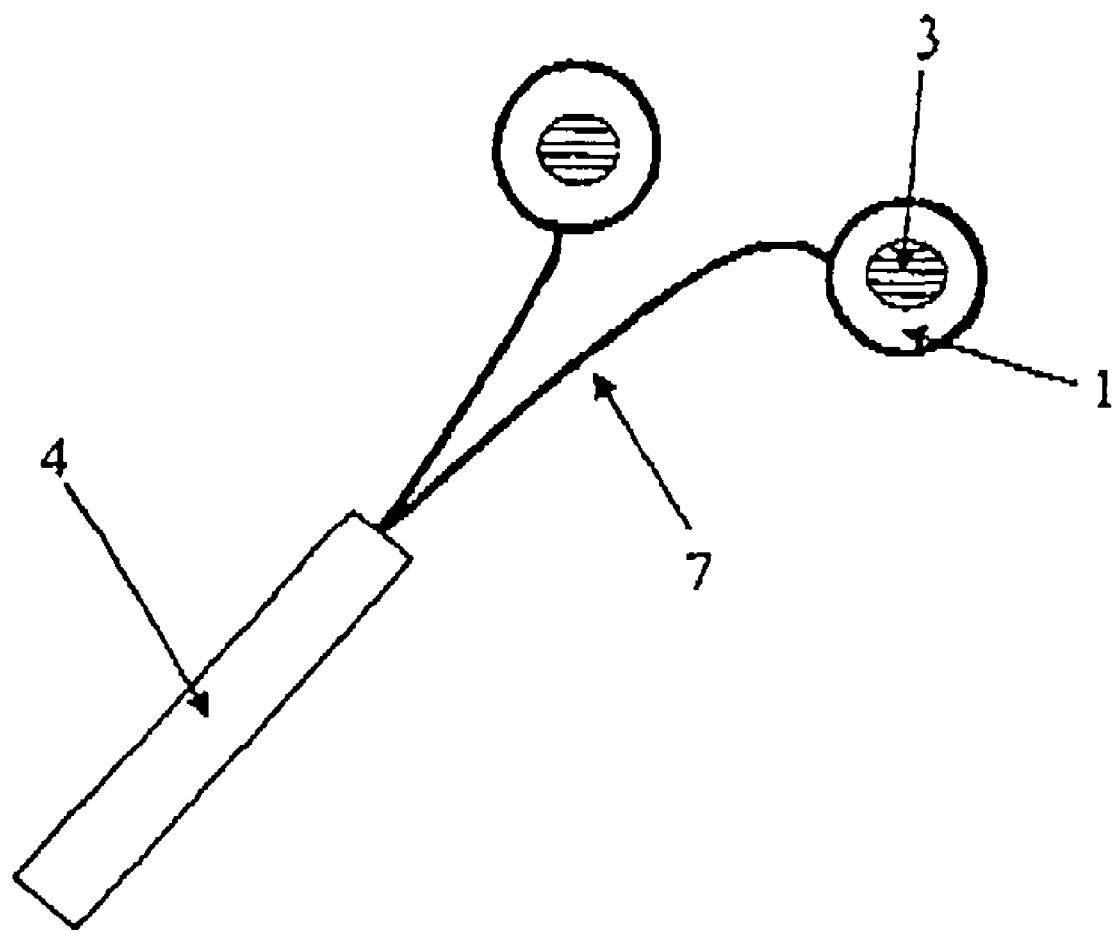
FIG. 3 is a schematic diagram of bases and conducting means of an example of an extraocular device of the invention, where the device includes of multiple bases, each base having a single electrode.

Turning now to FIG. 3, a further examples of an extraocular device of the present invention is illustrated in which the device consists of multiple bases 1, each of which have a single electrode 3 and are implanted independently. Independent insulated conductors 7 from these bases 1 converge to form the conducting means 4.

Figure 4A:
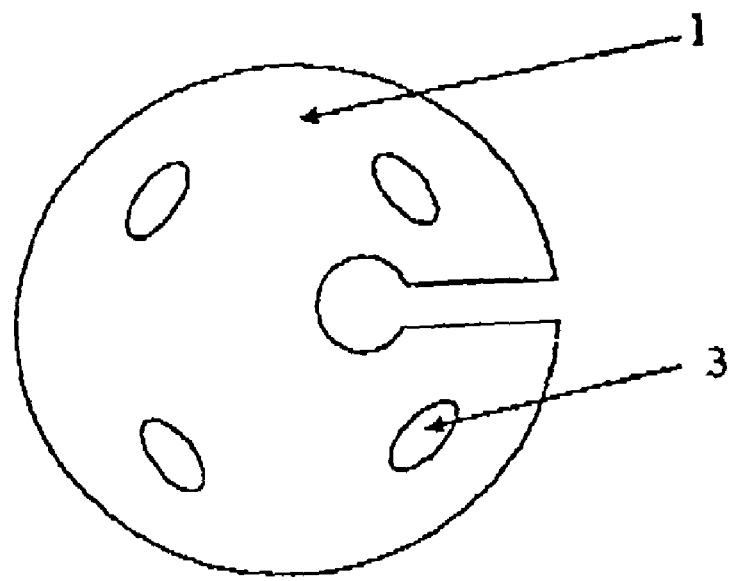
FIG. 4A is a plan view of the scleral-contacting surface of the base of an example of a device of the invention, where the base has 4 electrodes of 2 mm diameter, one placed in each quadrant.
Figure 4B:
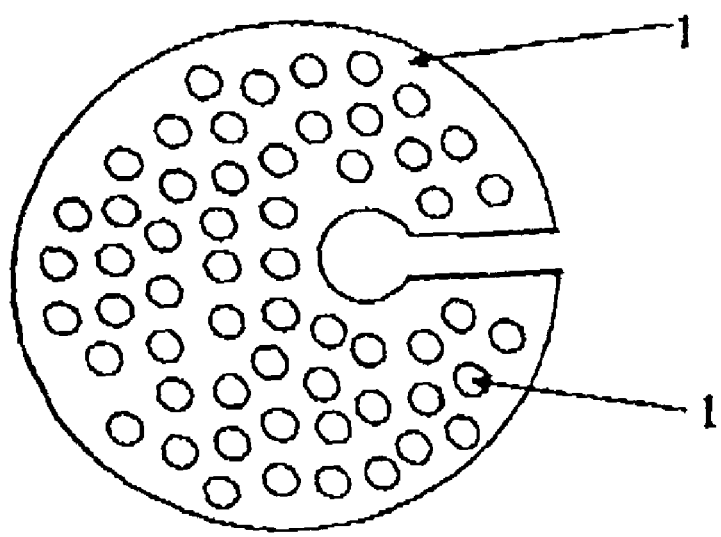
FIG. 4B is a plan view of the scleral-contacting surface of the base of an example of a device of the invention, where the base has 57 electrodes each of 700 μm diameter.

Examples of the device will now be described with reference to FIGS. 4A and 4B, which show front-on views of the inner scleral surface of the base member 1. The base member 1 may contain one or many hundreds of electrodes, the electrodes being generally denoted as 3, or any number in between. The electrodes 3 can be of varying diameters, arrangements or inter-electrode separations. FIG. 4A shows an extraocular device having a base member with 4 electrodes of 2 mm diameter, one placed in each quadrant. FIG. 4B shows an extraocular device having a base member with 57 electrodes, each of 700 µm in diameter.

Figure 5:
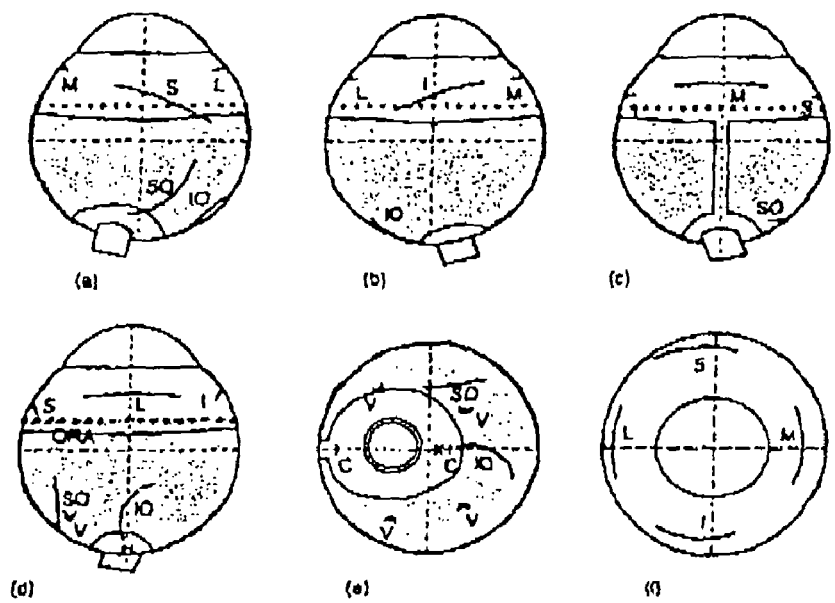
FIG. 5 is a schematic representation showing example methods for placing the base of devices of the invention on the eye.

Turning now to FIG. 5, there are depicted six exemplary methods of placement of the base member of examples of devices of the invention on the eye. FIG. 5a shows placement of the device from above the eye; FIG. 5b depicts placement of the device from below the eye; FIG. 5c illustrates placement of the device from the medial side of the eye; FIG. 5d illustrates placements of the extraocular device from the lateral side of the eye; FIG. 5e shows placement from behind the eye; and FIG. 5f shows placement of the example device from the front of the eye. The base member is slid over the scleral surface of the posterior half of the globe of the eye. The anterior extent of the base member stops behind the attachment of the rectus muscles. This is also the approximate region where the sensory neuroretina ends (ora serrata). According to this example, a defect or elongated aperture in the posterior portion of the base member allows passage of the optic nerve and long ciliary vessels. In this example, the base member has a slit at its medial aspect; this allows it to be slid over the eye from a lateral approach to form a sleeve around the eye.

Figure 6:
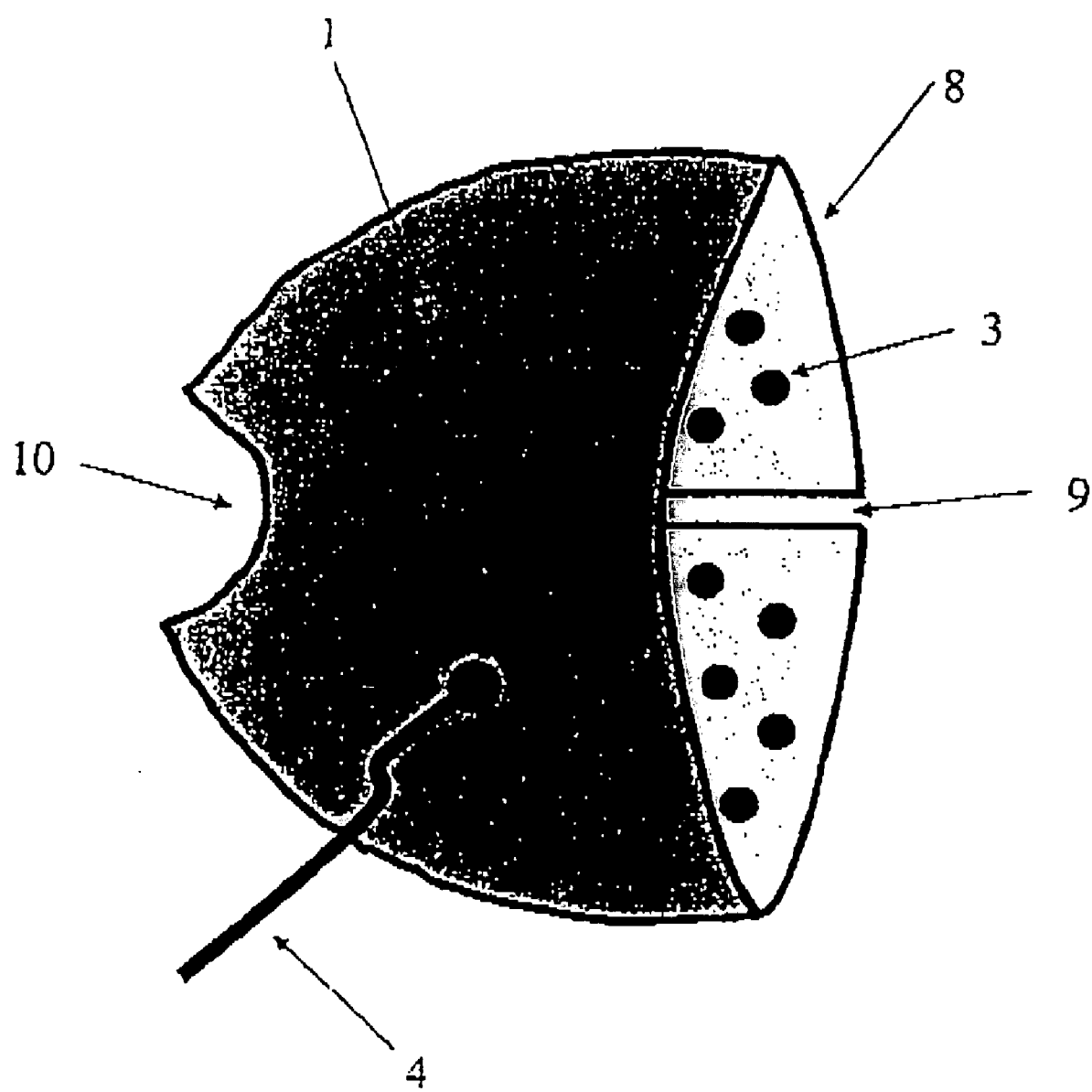
FIG. 6 is a schematic representation showing an enlarged side-view of the base and conducting portion of an examples of a device of the invention.

FIG. 6 illustrates an enlarged view of an example of a device of the invention with particular emphasis on the base member 6 of this embodiment, showing its anterior 8, posterior 10, and medial 9 defects, which have special relations to its positioning and relation to the anatomical structures of the globe of the eye. The electrodes of the base 6 of the device are generally indicated as 3.

Figure 7:
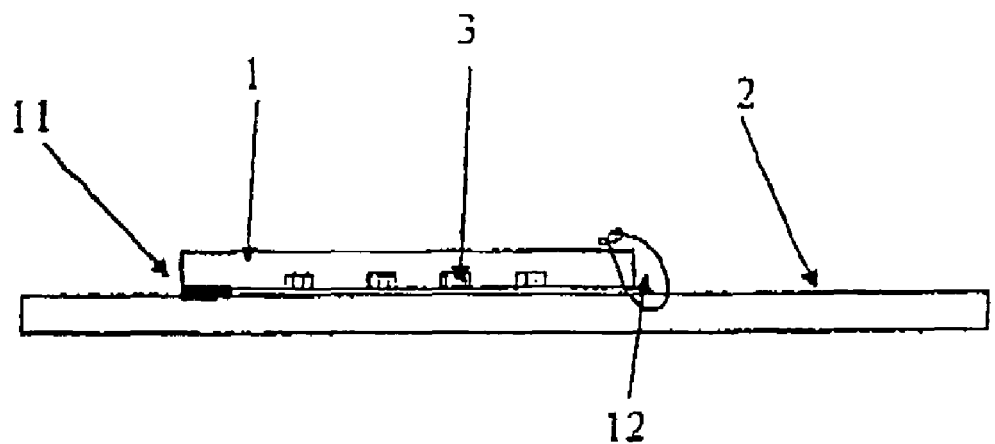
FIG. 7 is a schematic representation showing sample attachments of a base of an example of the extraocular device of the invention to the scleral surface of the eye.

Turning now to FIG. 7, there are illustrated exemplary means of attachment of the extraocular devices of the invention to the scleral surface of the eye. In particular, the electrodes 3 are placed to make contact with the scleral surface of the eye 2. The base or base member 1 can be secured to the eye either through the use of sutures 12, or through the use of a suitable bioadhesive glue 11, as discussed above, between the edges of the base or base member 1 and the scleral surface of the globe. Alternatively the base member 1 may stay attached to the scleral surface of the globe without these methods when its shape conforms to the shape of the globe and holds it in position.

Figure 8:
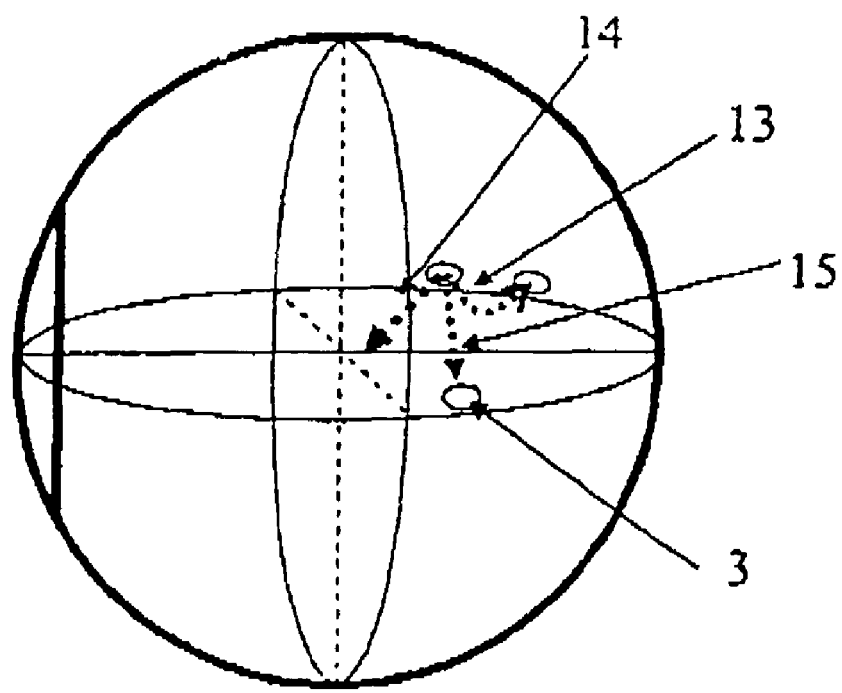
FIG. 8 is a schematic representation showing sample methods for electrical stimulation of the eye with electrodes of an example of an extraocular device of the invention.

FIG. 8 shows examples of certain methods for electrical stimulation of the eye with an extraocular device of the invention. A stimulating electrode can be stimulated with respect to a distant ground electrode 3 (monopolar); it can be stimulated with respect to another electrode nearby 13, 14, (near-bipolar). It can be stimulated with respect to a distant electrode 3 (distant-bipolar). It can also be stimulated with respect to multiple other electrodes (multipolar mode).

Figure 9A:
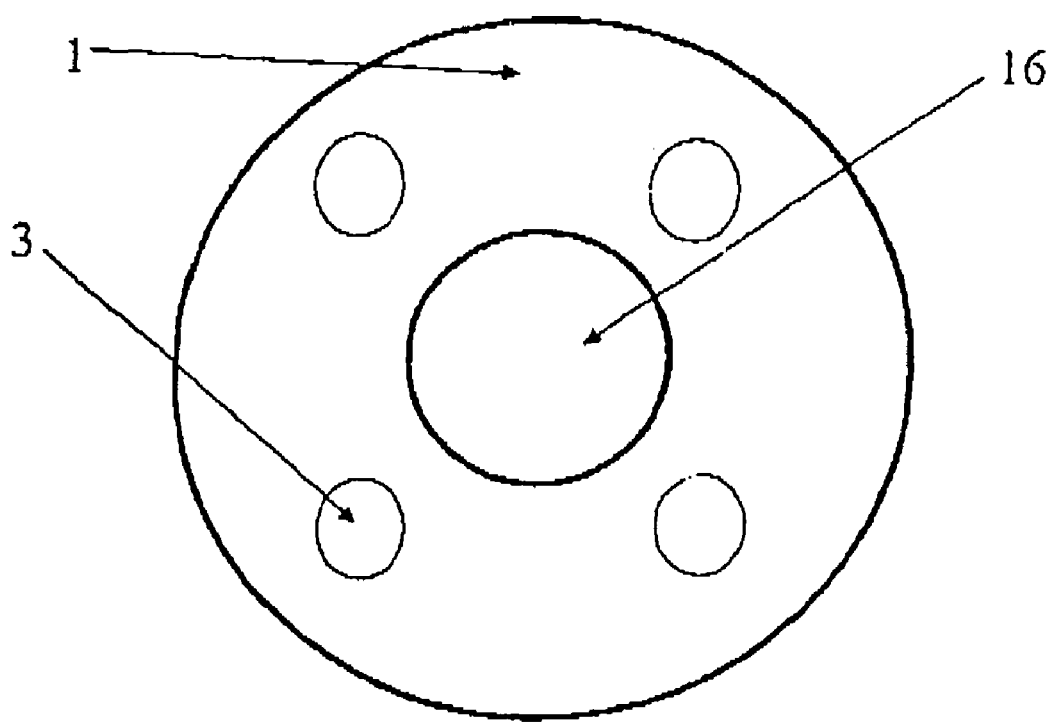
FIG. 9A is a schematic representation of the scleral-contacting surface of the base of an example of a device of the invention, where the base is perforated to decrease the degree of separation of connective tissues from the sclera of the eye.

FIG. 9A shows a further example of the device in which a perforations 3 in the base member 1 are used to decrease the degree of separation of connective tissues overlying the sclera of the eye from the sclera of the eye. The approximate location of the optic nerve as it exits from an aperture in the extraocular device is generally indicated as 16. Such perforations 3 decrease the thickness profile of the device, and thereby cause a minimal disruption between the scleral surface of the eye and the overlying connective tissue surrounding the globe of the eye, such as the fascia bulbi/tendons of the capsule (not shown).

Figure 9B:
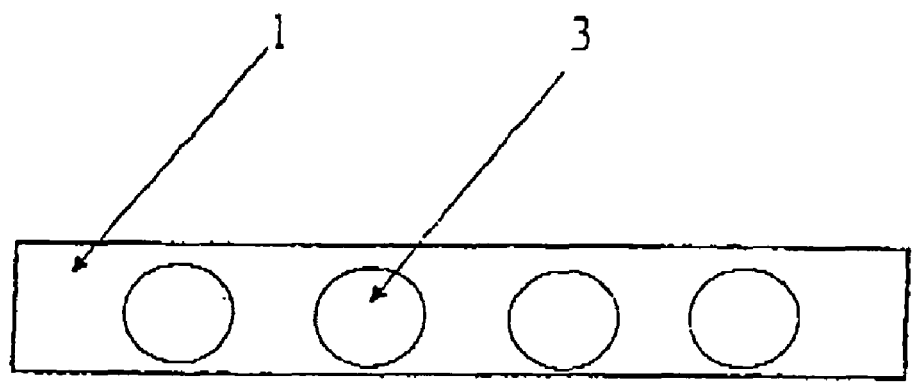
FIG. 9B is a schematic representation of the base of an example of an extraocular device according to the invention, where the base is in the form of a linear array of electrodes in a strip.

A further example of an extraocular device of the invention is shown in FIG. 9B, in which the base member 1 is in the form of a linear array of electrodes 3 in a strip.

Figure 10:
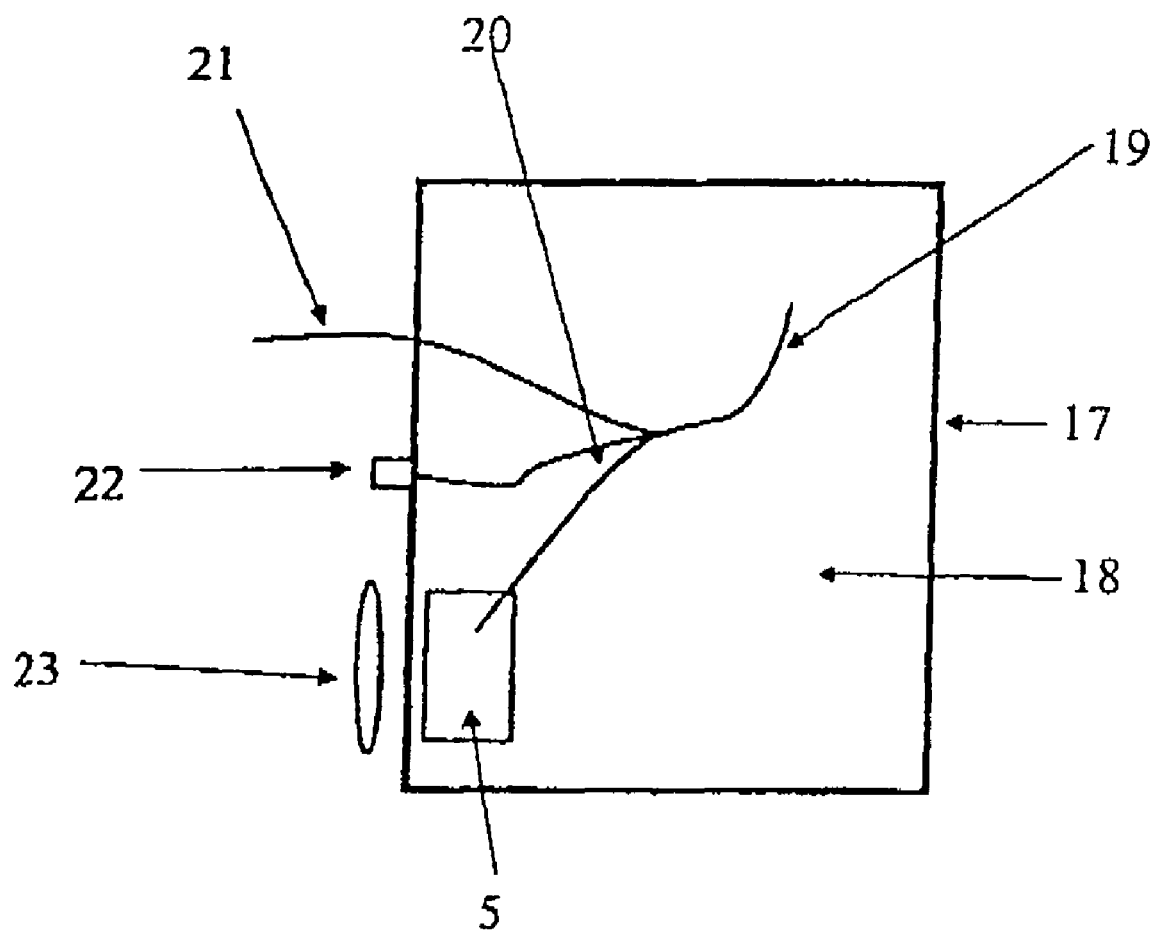
FIG. 10 contains schematic representations of extraocular devices of the invention illustrating variations for termination of the conducting means of the devices.

Yet a further example of an extrocular device of the invention is shown in FIG. 10, shows the options for termination of the conducting means 19 into the stimulator. The conducting means may connect to an internal stimulator 5. Alternatively, the conducting means may connect to a percutaneous plug 22 by extension of the conducting means 20, or it may exit the body percutaneously 21. The internal body compartment is generally indicated as 18, the external body compartment is generally indicated as 17. The internal stimulator 5 may be powered and controlled by an inductive link from a transmission coil 23 that has been placed outside the body.

In order that the invention may be readily understood and put into practical effect, particular preferred embodiments will now be described by way of the following non-limiting examples.

EXAMPLES

Example 1

Development of a Retinal Prosthesis for Blind Patients Based on Extraocular Stimulation of the Eye with Disc Electrodes The present study was undertaken to investigate the feasibility of an extraocular approach to retinal stimulation. This is the first study of an extraocular retinal prosthesis, an approach to visual prosthesis development for which a device has hitherto not yet been developed (Maynard, 2001, above; Margalit et al., 2002, above; Humayan et al., 2003, above). The present inventors intend to adapt the neuroprosthetic technology that is available in the Nucleus 24 Auditory Brainstem Implant (Cochlear Ltd, Australia). This implant has an electrode array of 21 platinum disc electrodes, each of 700 μm diameters, with a 950 μm centre-to-centre inter-electrode spacing, arranged in 3 rows in a silicone carrier. A number of electrode types, configurations, and stimulus methods were investigated to optimise the development of an extraocular retinal implant for the restoration of visual perception to blind patients.

Materials and Methods

Acute experiments were carried out in anaesthetised cats in accordance with the approval and guidelines of the animal ethics committee of the University of New South Wales. In adult cats (n=6) weighing between 2.5 kg and 5.5 kg, anaesthesia was induced with an intramuscular injection of ketamine (20 mg/kg) and xylazine (1 mg/kg). The animals were given a preoperative dose of subcutaneous atropine (0.2 mg/kg) and dexamethasone (1.5 mg/kg). After intubation the animals were ventilated, and anaesthesia was maintained with a 70:30 mixture of nitrous oxide and oxygen, with 0.5-1% halothane. ECG, end-tidal carbon dioxide, and core body temperature monitoring was carried out, and animals were monitored regularly for the absence of reflexes to ensure adequate anaesthesia. At the end of the experiment the cat was euthanased with an intravenous injection of pentobarbital. The cats underwent a bilateral craniotomy of the parietal bones, and the dura was removed to expose the primary visual cortex (cytoarchitectonic area 17) of both hemispheres. The right orbit was approached by removing the bone of the lateral orbital wall and retracting or removing the right temporalis muscle. The cerebral cortex was regularly irrigated with warmed (35° C.) paraffin oil.

Recordings of cortical evoked potentials were carried out after placement of the cat in a stereotaxic frame, with platinum or silver ball electrodes placed on the pial surface of the primary visual cortex. Cortical potentials were recorded using Scope 3.6.11 software and a PowerLab/4SP data acquisition system connected to a ML135 Biopotential Amplifier (ADInstruments, Australia). Evoked potentials were averaged over 100-200 trials, after being filtered to within a frequency range of 10 Hz-5 kHz, and a 50 Hz notch was used. A differential recording system was used, with an indifferent scalp clip and ground connected to a right thigh subcutaneous pin.

A variety of stimulating electrodes and configurations were investigated. This included silver ball electrodes (1 mm diameter), flat platinum disc electrodes of 2 mm and 4 mm diameters (Cochlear Ltd, Australia), and a multi-electrode array consisting of 21 platinum disc electrodes each of 700 μm in diameter (Cochlear Ltd, Australia), which were embedded in a scleral buckle and implanted in the same manner as standard scleral buckles. In some experiments a contact lens electrode was used as the stimulus return path (ERGjet; Universo, Switzerland).

Electrical stimuli were rectangular constant-current symmetrical biphasic pulses (delivered from a 2100 Isolated Pulse Stimulator; AM-Systems, USA) or monophasic pulses (from a ML180 Stimulus Isolator; ADInstruments). Biphasic stimuli were also delivered using a Nucleus 24 ABI (Cochlear Ltd, Australia).

Averaged cortical response to electrical stimulation of the right retina with extraocular electrodes was recorded, and compared a variety of configurations. VEP and ERG recordings were obtained to confirm the integrity of the neural visual pathway, and trialed surgical implantation techniques for an electrode array.

Results

Ball Electrodes

Figure 11:
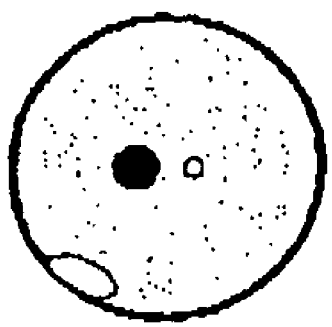
FIG. 11 is a schematic representation of posterior views of the right globe showing the placement of ball electrodes in Cats A and B.
Figure 11:
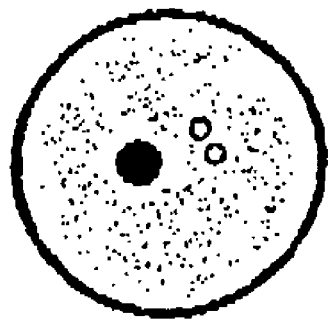

Monopolar and bipolar extraocular stimulation of the retina were investigated with silver ball electrodes. In Cat A the stimulation electrode was placed on the posterior scleral surface of the eye, 5 mm lateral to the optic nerve attachment, in the horizontal meridian. In this animal a 4 mm platinum disc electrode was implanted on the inferionasal aspect of the globe to serve as the current return path. In Cat B, two silver ball electrodes with a 5 mm inter-electrode spacing were placed at the central posterior surface of the globe superiolateral to the optic nerve head. This is illustrated in FIG. 11, where the solid circle represents the attachment of the optic nerve to the back of the eye. Open circles represent the placement of electrodes.

Figure 12:
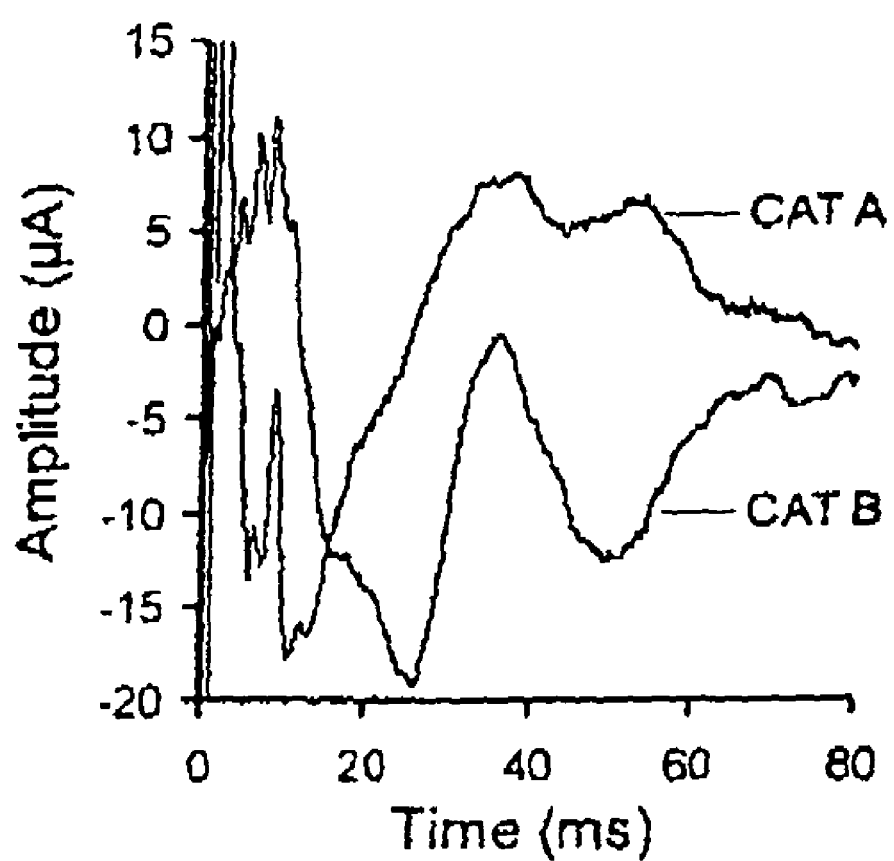
FIG. 12 is a graphical representation illustrating evoked response at the primary visual cortex to retinal stimulation with 1 mA stimuli of 400 μs phase duration.

The typical electrical evoked response to cathodal-first biphasic stimulation in a monopolar configuration from Cat A, was compared to the response from monophasic stimulation of bipolar electrodes in Cat B (FIG. 12). Bipolar stimulation in Cat B showed a typical negative-positive electrically evoked response (Dawson & Radtke, Invest Ophthalmol Vis Sci 1977; 16(3):249-52). However due to a prolonged artifact in Cat A, as is typical with monopolar stimulation (Yeomans, Principles of Brain Stimulation. New York: Oxford University Press, 1990), the initial negative component of the cortical response in this cat was obscured (a comparison with control waves was performed). The first visible true response in Cat A is a positive peak at 38 ms. A second positive peak follows this wave at 54 ms. The average latency of the negative and positive peaks for Cat B, and the two positive peaks for Cat A are shown in Table 1:

TABLE 1

Latency of the cortical evoked response to extraocular stimulation of the retina in Cat A and B. The initial negative peak in Cat A is obscured due to a prolonged stimulus artifact from monopolar stimulation. Cat A exhibited two defined positive peaks, whereas Cat B (bipolar stimulation) exhibited a single early positive peak.

| Latency/SD | N1 (ms) | P1 (ms) | P2 (ms) |
|---|---|---|---|
| Cat A | — | 36.53/1.83 | 51.70/2.37 |
| Cat B | 27.32/1.42 | 40.85/3.48 | — |

Figure 13:
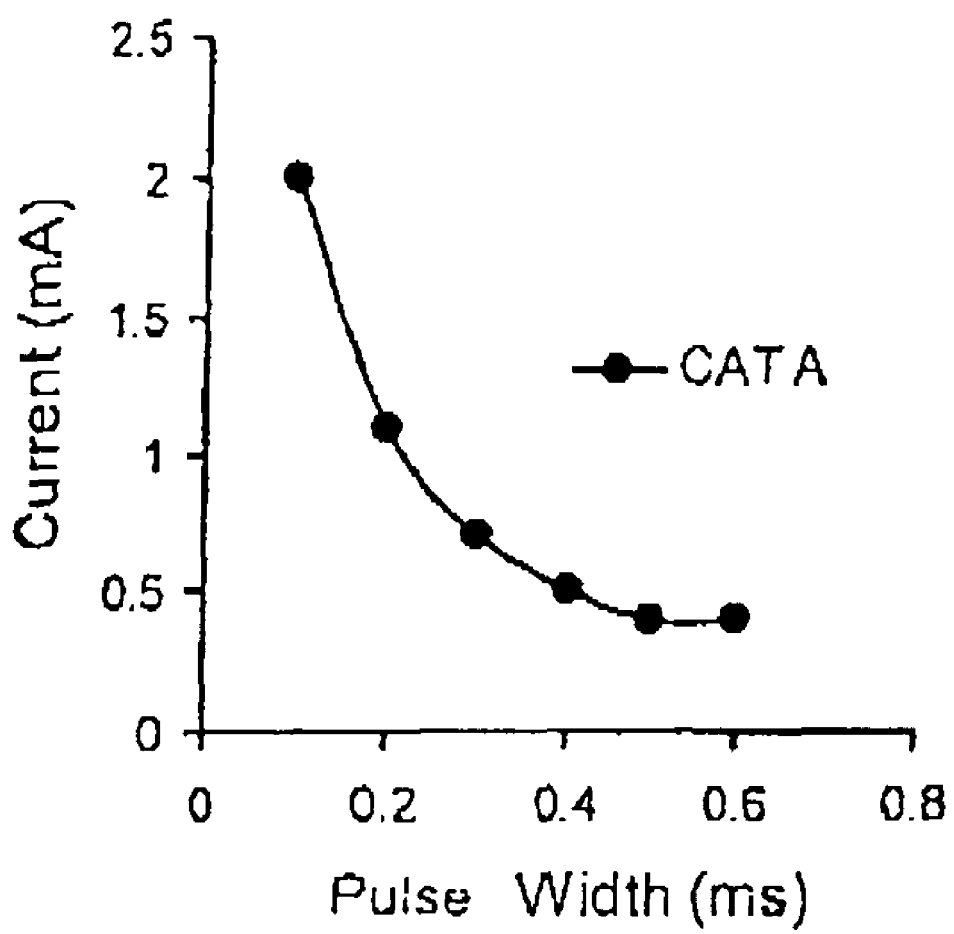
FIG. 13 is a graphical representation of the strength-duration curve for extraocular retinal stimulation with biphasic cathodal-anodal symmetrical pulses in a monopolar configuration.
Figure 14:
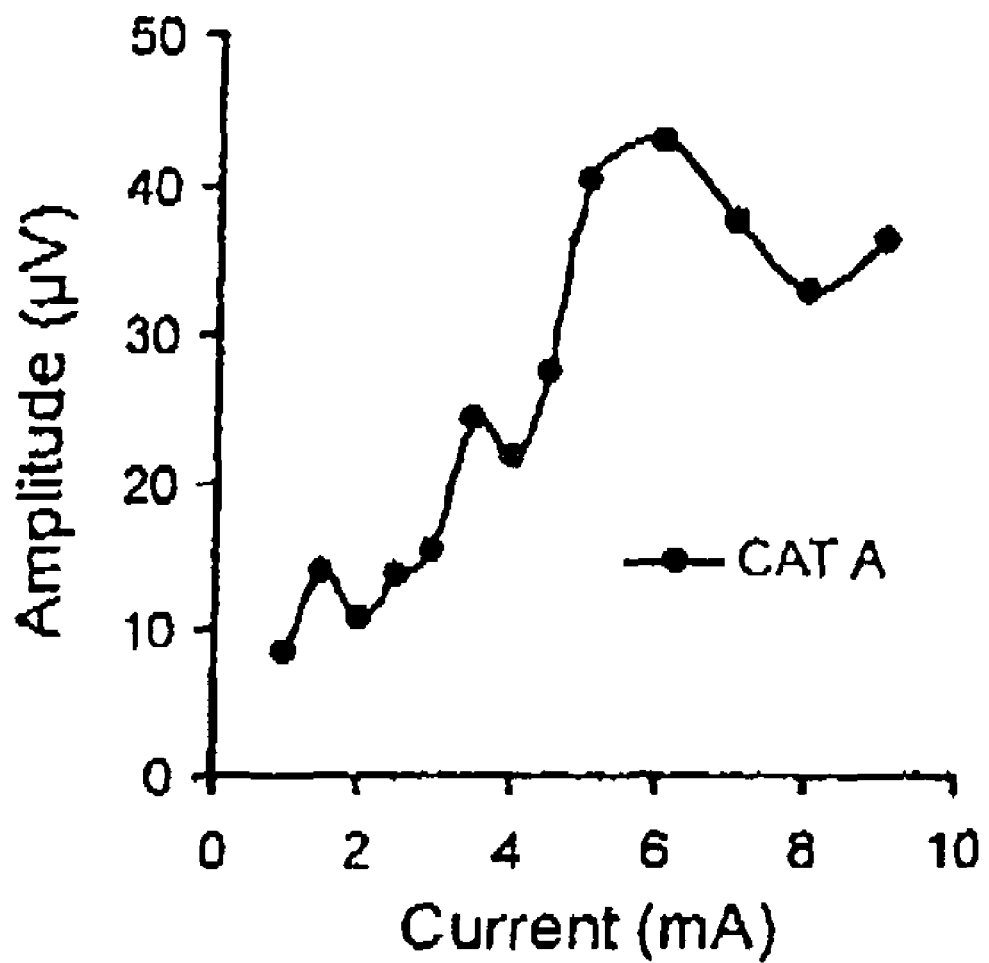
FIG. 14 is a graphical representation showing amplitude of the positive peak of the cortical evoked response to extraocular retinal stimulation with 250 μs cathodal-first biphasic pulses.

By determining the threshold current to elicit a response at the visual cortex, a strength-duration curve was obtained for biphasic monopolar extraocular electrical stimulation of the retina (FIG. 13). For phase durations greater than 200 µs, threshold currents for eliciting a visual cortex response were below 1.5 mA. We also determined the peak amplitude of the positive component of the evoked response in Cat A for a range of stimulus current levels at a pulse width of 250 µs (FIG. 14). Higher response amplitudes were obtained with increasing current up to 5 mA, after which there was a response plateau.

Multi-Pulse Studies

The effect of pulse trains on cortical response amplitude was investigated. The amplitude of the positive wave of the electrical evoked response was recorded for 2 mA, 250 µs cathodal-first biphasic stimuli to single pulses and pulse trains of 2, 3 or 4 pulses presented at 200 Hz. These responses were also compared to the amplitude of the cortical potential evoked by a double pulse at 100 Hz (FIG. 5). The highest cortical responses were obtained with three pulse trains. For double pulses, a longer interval between pulses evoked a larger cortical response.

Cortical Activation Map

Figure 16:
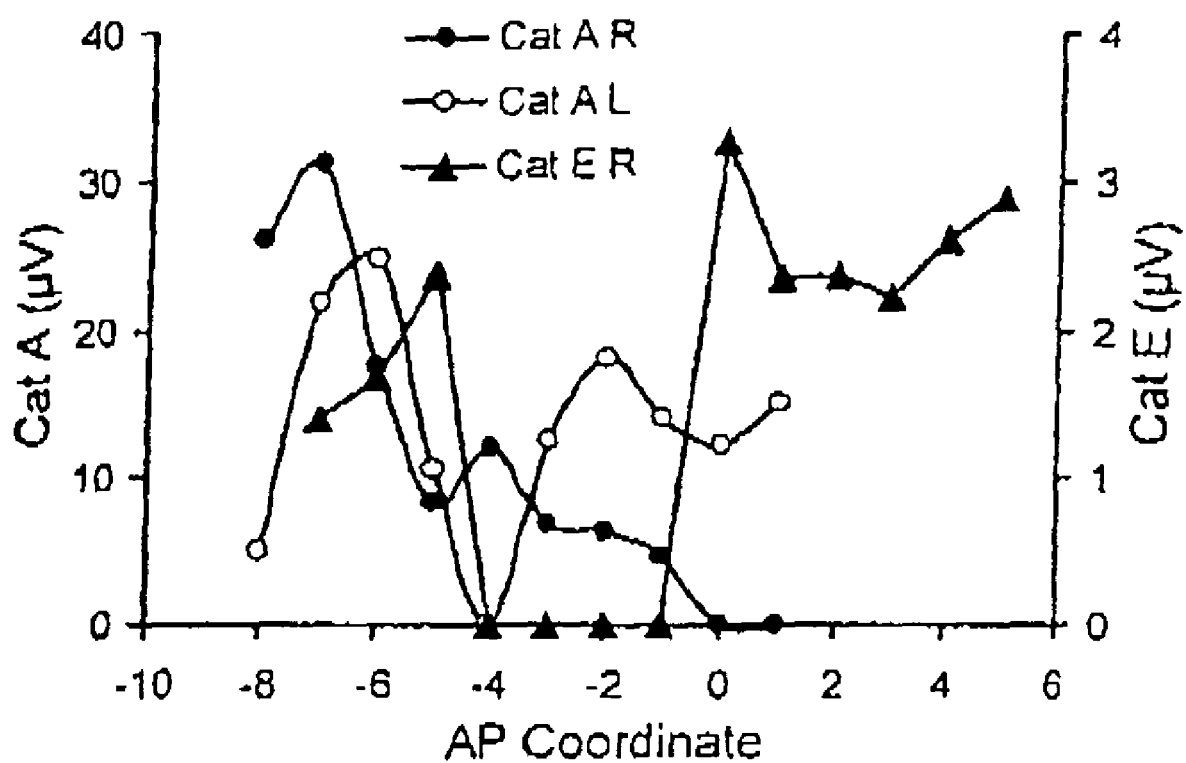
FIG. 16 is a graphical representation showing bilateral cortical activation map for monopolar stimulation of the retina with an extraocular electrode placed 5 mm lateral to the optic nerve attachment in the horizontal meridian (Cat A). Also shown is the right cortex activation map for electrical stimulation with disc electrodes in Cat E (see FIG. 7). The X-axis denotes Horsely-Clarke coordinates from 5 (A5) to −8 (P8).

Extraocular stimulation of a localised region of the sclera leads to excitation of a localised region of the retina which evokes localised cortical responses. Monopolar extraocular stimulation of the retina was undertaken with a ball electrode placed in the horizontal meridian 5 mm lateral to the attachment of the optic nerve on the globe. Biphasic pulses of 250 µs pulse width and 2 mA current intensity were used, and recorded evoked responses at localised points on the primary visual cortex over the posteriomedial regions of the lateral gyri of both hemispheres. Using a 1 mm silver ball recording electrode we moved antero-posteriorly in 1 mm steps to record evoked cortical potentials from Horsely-Clarke co-ordinates A1 to P8. We recorded from the most medial position of the superior surface of the lateral gyrus that was accessible after a craniotomy preserving a narrow strip of bone overlying the sagital sinus (FIG. 16).

Cortical responses in Cat A were localised in the anterio-posterior plane to Horsely-Clarke co-ordinates P6 and P7 in the left and right hemispheres respectively. There was a second smaller peak of cortical activity anteriorly in the left hemisphere at P2, which was not present in the right hemisphere.

Disc Electrodes

Figure 17:
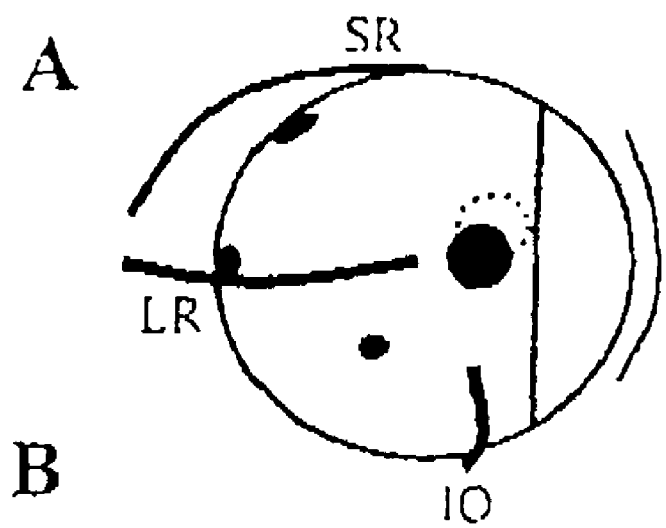
FIG. 17A is a schematic representation showing three configurations of electrode placement on the eye.
FIG. 17B is a picture of the right eye in Cat D after implantation of the electrodes and suturing the electrode tails to the periorbita.
Figure 17:
Figure 18:
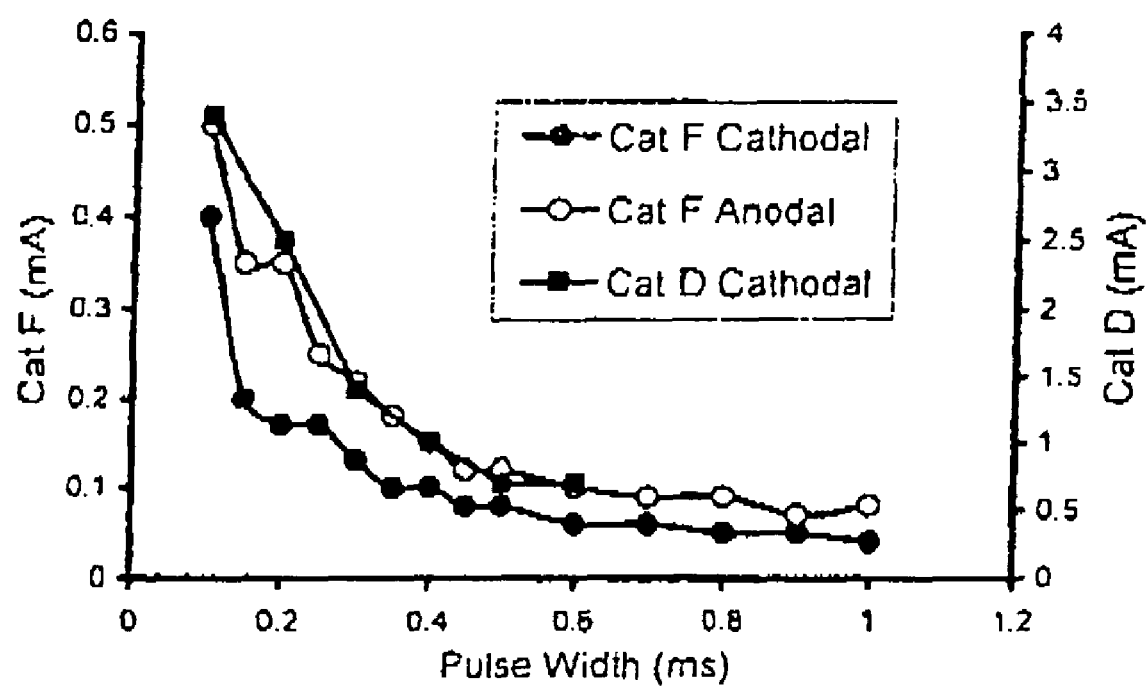
FIG. 18 is a graphical representations of strength-duration curves for Cat D and Cat F.

Extraocular stimulation of the retina with flat platinum disc electrodes in 3 different configurations was investigated (FIG. 17A). In Cat D, a 2 mm active electrode was sutured under the superior rectus muscle and a 4 mm return electrode was placed anterior to the attachment of the lateral rectus muscle (FIG. 17B). In Cat E, a 2 mm active electrode was placed in the inferio-lateral quadrant of the right eye and a 4 mm return electrode was placed anterior to the attachment of the medial rectus muscle. In Cat F, a 2 mm platinum disc was applied to the sclera 5 mm lateral to the optic nerve attachment in the horizontal meridian and a contact-lens electrode applied to the cornea was used for the current return path. The strength-duration curve for cortical activation with the electrode configurations in Cats D and F is shown in FIG. 18. Electrical stimulation of the eye in Cat E produced a right cortex cortical activation map which is shown along with Cat A in FIG. 6. Anodal stimulation was more effective than cathodal stimulation at exciting the retina (Cat F), demonstrated by the upward shift of the strength-duration curve. The strength-duration curves flattened towards rheobase at pulse widths greater than 500 µs.

Increasing the pulse width of the stimulus up to 1 ms, led only to small decreases in the threshold current required for retinal activation. Cathodal stimulation with the electrode configuration of Cat F was more effective than the configuration used in Cat D. In Cat F, it was possible to obtain cortical responses from retinal stimulation with threshold currents of less than 100 µA at pulse widths greater than 400 µs.

Multi-Electrode Array

Extraocular retinal stimulation with components of a prototype extraocular retinal prosthesis in two cats was undertaken. In Cat C we implanted a 21-electrode array, embedded in a scleral bukcle, along the horizontal meridian of the posterior sclera of the right globe, and bipolar biphasic pulses were delivered with a bench stimulator. In Cat F, extraocular stimulation of the retina was carried out with a Nucleus 24 ABI, using Neural Response Telemetry (NRT) software and the Portable Programming System (PPS) (Cochlear Ltd, Australia).

Figure 19:
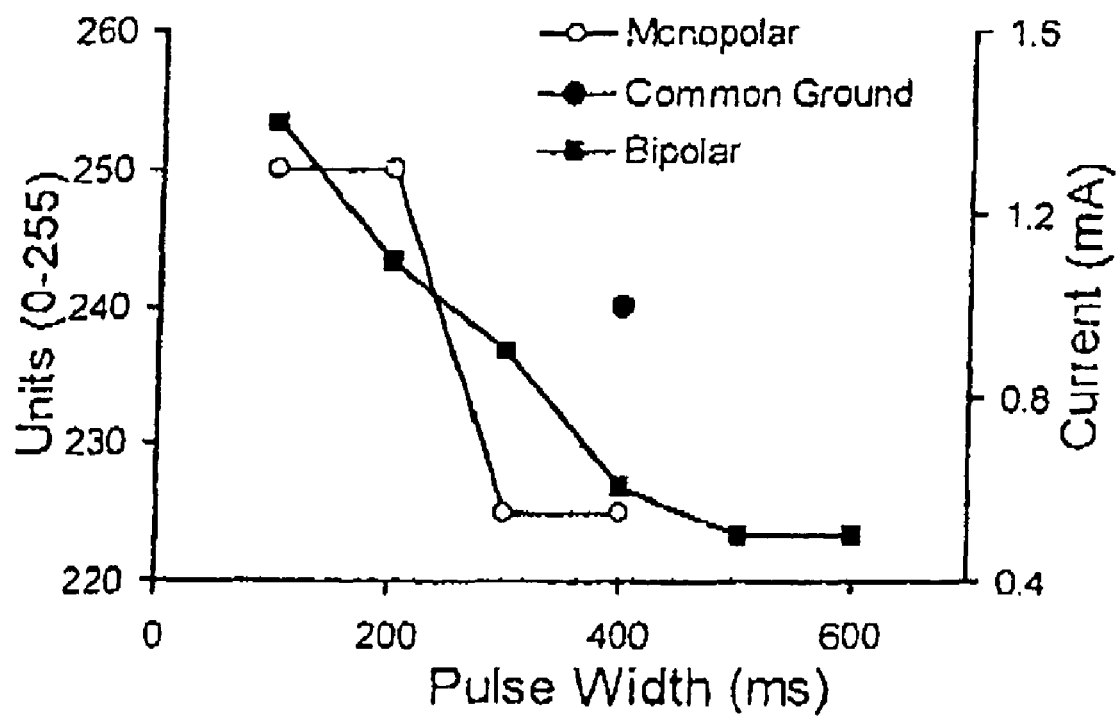
FIG. 19 is a graphical representations of strength-duration curves for scleral stimulation with a 21-electrode array.

Strength-duration curves for both bench and implant stimulation are shown in FIG. 19. Electrode impedance measurements obtained with the reverse telemetry feature of the implant (Cat F) gave a reading of 15.6 kOhms in the monopolar configuration (single grid electrode active, contact lens electrode as the corneal return) and 8 kOhms in the "common ground" configuration (single electrode active, all other 20 electrodes on the grid shorted to the return path).

Using bipolar stimulation (bench) of the electrode array, threshold currents were lower than 1 mA for pulse durations greater than 300 µs. Stimulation levels with the implant are programmed in device units up to "255", which is the strongest stimulation level using the unit, and equal to approximately 1.75 mA. Pulse widths up to the device maximum of 400 µs were investigated. Monopolar stimulation was more effective than common ground mode stimulation. No responses could be elicited with a pulse width below 400 µs in common ground mode. In monopolar configuration, using pulse widths of 100 µs and 200 µs, stimulation intensities at the upper limits of the device were required.

Discussion

Electrical stimulation of the retina can elicit visual perceptions in blind patients 9, commonly described as small spots of light termed "phosphenes". Major efforts are underway to develop a retinal prosthesis that will hopefully restore a level of visual perceptions that will be functionally useful to blind patients (Rizzo et al., 2001; Margalit et al., 2002; Humayun et al., 2003; Eckmiller, *Ophthalmic Res* 1997; 29(5):281-9; Jensen et al., 2003). A medical device for this purpose must be surgically feasible (Walter et al., Retina, 1999; 19(6):546-52), be physically biocompatible to the body (Majji et al., *Invest Ophthalmology & Vis Sci* 1999; 40(9):2073-81), utilize safe stimulation parameters (McCreery et al., *IEEE Transactions on Biomedical Engineering* 1990; 37(10):996-1001; Agnew & McCreery, *Epilepsia* 1990; 31(Suppl 2):S27-32), and give the highest possible number of stable, reproducible and resolvable phosphene sensations (Humayun. 2001, above). The present inventors believe that an extraocular approach to retinal prosthesis development will be better than current attempts at epiretinal prostheses (Margalit et al., 2002, above; Humayun et al., 2003, above), for fulfilling these goals in the development of a clinically viable visual prostheses for blind patients in the short term.

In six cats it was possible to record evoked responses at the visual cortex to electrical stimuli applied to the retina with electrodes placed on the posterior surface of the globe (FIG. 11). We investigated electrical stimulation with different electrode types in a variety of configurations (FIG. 17A), all of which were able to evoke visual cortex responses. As it has been postulated that activity at the primary visual cortex is correlated to conscious perception (Lamme et al., *Vision Res* 2000; 40(10-12):1507-21), the activity evoked in the visual pathway through this method of stimulation will most probably evoke phosphene perception in human patients.

The feasibility of implanting both electrode arrays, and single electrodes, on the surface of the sclera was also investigated. In the cat shown in FIG. 17B, the disc electrode was slipped under the superior rectus muscle, and the electrode tail was then sutured to this muscle, and then again to the periorbita with a purse-sting suture. Local paralysis of the extraocular muscles to prevent movement will be necessary in future chronic implantations. It would also be possible in the future to use biological adhesives or sutures to fix the silicone base carrying the electrode directly to the sclera. The placement of extraocular electrodes does not require any intraocular surgery, or the intraocular placement of foreign bodies against the delicate retinal tissues. It also does not require complicated methods of attachment of electrode arrays to the retinal surface such as tacks (Humayun et al., 2003, above). Extraocular electrodes have a better surgical feasibility profile than intraocular electrodes.

The minimum thresholds for eliciting cortical evoked responses with extraocular electrodes were examined. Current thresholds were variable amongst cats with different electrode configurations. The lowest thresholds were found with a 2 mm electrode placed on the posterior of the globe, and stimulated with respect to a contact lens electrode placed on the cornea. The threshold for eliciting an evoked response was as low as 100 µA (FIG. 18) at a pulse duration of 400 µs (0.04 µC per phase). This translates to a charge-density at the electrode surface of 1.27 µC/cm2, which is well within safe charge injection levels in human studies for chronic neural stimulation (Gordon et al., *Electroenceph & Clin Neurophysiol* 1990; 75(5):371-7).

Higher thresholds occurred with monopolar stimulation using the Nucleus 24 ABI (FIG. 19). A threshold of 225 Device Units (255 Units=1.75 mA) was obtained when using 400 µs cathodal-first biphasic pulses. With extraocular stimulation, the electrodes are not applied directly on top of the delicate retinal tissue. The firm scleral base for extraocular electrodes avoids mechanical trauma to the retina, and decreases the likelihood of pathological effects due to charge transfer and heat generation (Jayaker, *Advances in Neurology* 1993; 63:17-27).

The ability of extraocular stimulation to produce localised phosphenes was assessed, by investigating whether extraocular stimulation produces localised activation at the primary visual cortex. The medial edge of the lateral gyrus (cytoarchitectonic area 17) contains a retinotopically mapped representation of the visual field (Tusa et al., *J Comp Neurol* 1978; 177(2):213-35). In Cat A the cortical response was localised posteriorly at a similar anterio-posterior coordinate in both hemispheres (FIG. 16).

Figure 15:
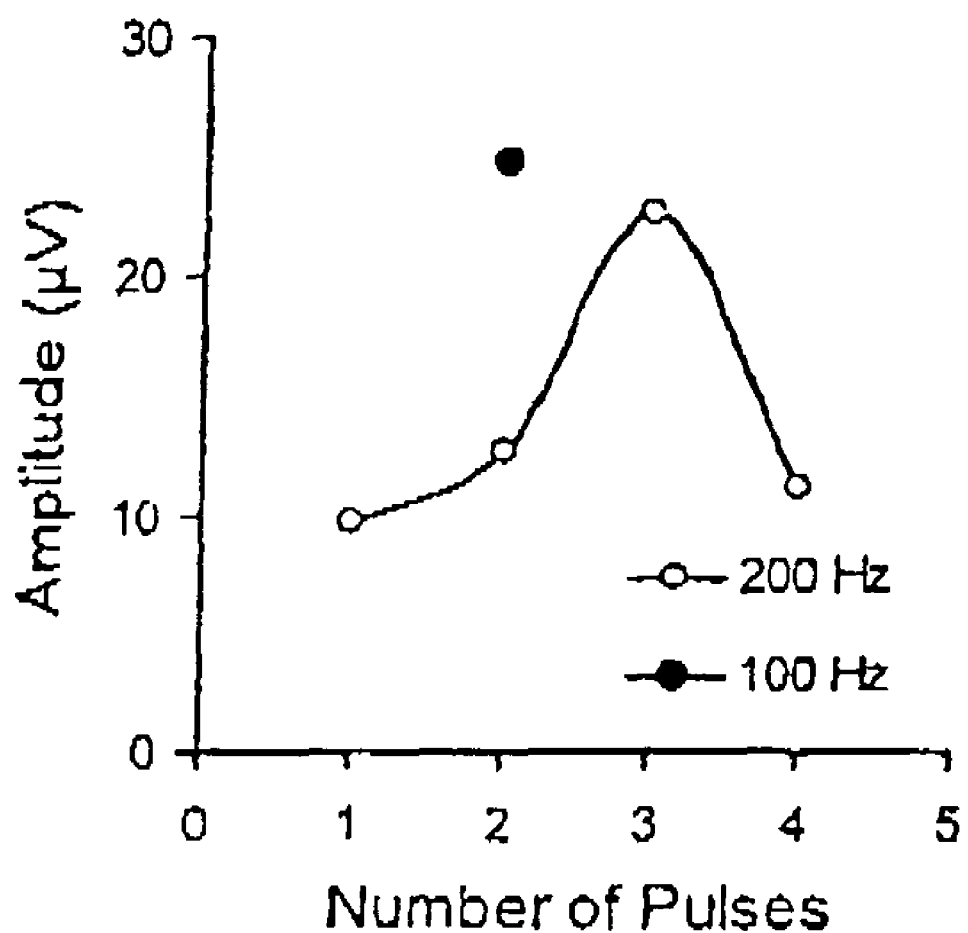
FIG. 15 is a graphical representation showing the effect of stimulus pulse trains on the electrically evoked response for frequencies of 100 Hz and 200 Hz.

Studies of pulse summation will aid in the identification of optimal stimulus parameters for an extraocular retinal prosthesis. Ideal frequencies for pulse trains were investigated with multi-pulse studies. Higher cortical responses were obtained with paired pulses at 100 Hz than at 200 Hz. For 200 Hz stimuli, peak responses were obtained with 3 pulse trains (FIG. 15). As expected, anodal stimuli were less effective than cathodal stimuli in eliciting extracellular stimulation of retinal tissue (FIG. 18) (Yeomans, 1990, above; Jayakar, *Advances in Neurology* 1993; 63:17-27). A basic feasibility study of adapting technology in the Nucleus 24 ABI for extraocular retinal stimulation was undertaken. This device is composed of an array of 21 platinum disc electrodes in a silicone carrier, and a stimulator implant which can be powered and controlled transcutaneously. The electrode array could elicit stimulation of the sclera under a variety of electrode configurations. The stimulator implant itself was able to evoked visual cortex responses with single biphasic pulses (FIG. 19).

An extraocular retinal implant will overcome many of the difficulties of using epiretinal stimulation for a visual prosthesis (Rizzo et al., 2001, above). The present inventors have shown the feasibility of such an approach by demonstrating an ease of surgical implantation, safe current thresholds for evoking cortical responses, and localised activation of the primary visual regions in the brain. Adaptation of the technology in the Nucleus 24 ABI will provide a basis for developing an extraocular prosthesis for human trial. It will provide a higher number of drivable electrodes (Dawson & Radtke, 1977, above), and hopefully resolvable phosphenes, than the epiretinal prostheses currently undergoing clinical trial (Humayun et al., 2003, above).

Example 2

Establishment of Suitable Threshold, Strength-Duration and Evoked Response Amplitude Data for Electrical Stimulation of the Retina with an Extraocular Device Materials and Methods Acute experiments were carried out in anaesthetised cats, with adherence to the ARVO statement for the use of animals in ophthalmic and vision research, the NIH principles of laboratory animal care and in accordance with the guidelines of the animal ethics committee of the University of New South Wales. In adult cats (n=3), anaesthesia was induced with an intramuscular injection of ketamine (20 mg/kg) and xylazine (1 mg/kg). The animals were given a preoperative dose of subcutaneous atropine (0.2 mg/kg) and dexamethasone (1.5 mg/kg). The pupils were dilated with atropine (1%) and phenylephrine (10%) eye drops. After intubation, the animals were ventilated and anaesthesia was maintained with a 70:30 mixture of nitrous oxide and oxygen, with 0.5-1% halothane. ECG, end-tidal carbon dioxide, and core body temperature monitoring was carried out, and animals were monitored regularly for the absence of reflexes to ensure adequate anaesthesia. At the end of the experiment the cat was euthanased with an intravenous injection of pentobarbital.

Two extraocular electrodes (manufactured for the study by Cochlear Ltd, Australia) were implanted on the right eye of each cat, one laterally and one superiorly. The extraocular electrode consists of a 2 mm diameter platinum disc (surface area 0.0314 cm$^2$) embedded on the surface of a silicone base shaped to conform to a portion of the outer scleral surface. A silicone tail was connected to the edge of the base within which was a helically wound (strain relief) electrode lead that was bonded to the inactive side of the platinum disc.

In each cat the right superio-lateral orbital wall was removed, and the periorbita in the horizontal plane laterally and vertical plane superiorly was incised 1 cm posterior to the limbus. The lateral and superior rectus muscles were removed to gain access to the sclera, and the electrodes were placed on the sclera and centred on points 13 mm posterior to the limbus with their tails pointing posteriorly. Using a 7-0 Vicryl spatula tip (Ethicon, USA), the extraocular electrode was attached to the sclera with 4 interrupted sutures distributed around its circumference, biting the silicone rim 1 mm from its edge. The periorbita and skin over the lateral orbit was then closed with the tails exiting through the posterior aspects of the wounds.

After implantation of the electrodes the cats were placed in a stereotaxic frame and a craniotomy of the right posterio-medial parietal bone was performed. The dura was removed to expose the posterio-medial lateral gyrus, over which the primary visual cortex is located. The exposed pial surface of the cerebral cortex was bathed in a well of warmed (35° C.) paraffin oil. Recordings of cortical evoked potentials were made with a 2 mm silver/silver chloride ball electrode. This was placed on the most medially accessible region of the pial surface of the lateral gyrus at Horsely-Clarke co-ordinates P2 or P3, the location of cytoarchitectonic area. A differential recording system was used with the indifferent electrode connected to a posterior scalp clip, and ground connected to a right thigh subcutaneous pin.

Cortical potentials were recorded using Scope 3.6.11 software and a PowerLab/4SP data acquisition system connected to a ML135 Biopotential Amplifier (all from ADInstruments, Australia). Evoked potentials were averaged over 200 trials, were filtered to within a frequency range of 10 Hz-5 kHz, and a 50 Hz notch was used.

Stimuli were generated with a PowerLab/4SP and were fed through a Model 2200 Analog Stimulus Isolator (AM-Systems, USA). Stimulation was performed with single biphasic charge-balanced constant-current pulses. A half-pulse of phase duration between 200 µs and 1000 µs was followed by an identical half-pulse of opposite polarity with an interphase interval of 100 µs. Current intensities between 10 µA and 3 mA were used. Stimuli were delivered at 2 Hz. Bipolar stimulation was performed between the lateral and superior extraocular electrodes, the polarity of the stimulus determined by the electrode polarity during the first phase of the stimulus. Monopolar stimulation occurred between the lateral extraocular electrode and a contact lens electrode (ERG-jet; Universo, Switzerland), which was used as the current return path. Stimulation was performed in the light-adapted eye.

Flash visual evoked potentials (VEPs) were recorded from the right eye after implantation of the electrodes. Flash stimuli were delivered from a Botex SP-106MR Super Strobe (N.C.W., Hong Kong) at 1 Hz, and the visual evoked response was averaged over 100 trials, with similar filter settings to those used for electrically evoked potential recording.

Results

Electrically Evoked Potential to Extraocular Stimulation

Figure 20:
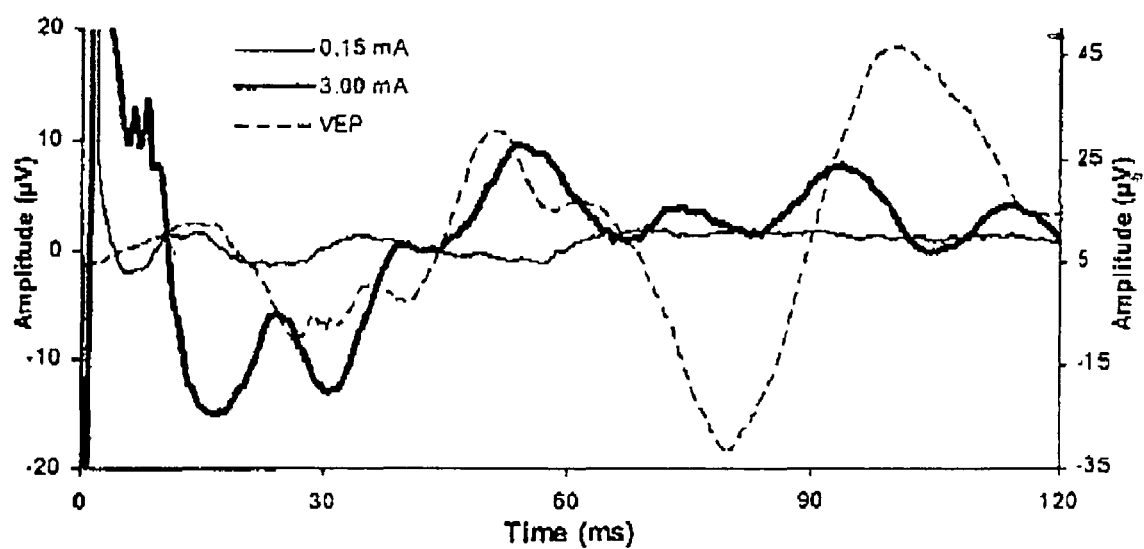
FIG. 20 is a graphical representation comparing cortical responses evoked from subthreshold (thin black line) and supra-threshold (thick black line) electrical stimuli with the visual evoked potentials to flash stimulation (broken line) in Cat 1.

The electrically evoked potential (EEP) to extraocular retinal stimulation is a complex wave consisting of early and late components. FIG. 20 shows the cortical response to sub-threshold (0.15 mA) and suprathreshold (3 mA) bipolar lateral-cathodal stimuli in Cat 1. Random cortical activity follows a subthreshold stimulus. An evoked wave was considered to be an EEP if its amplitude was at least twice the amplitude of the average baseline activity to subthreshold stimuli, and exhibited typical EEP latencies. The early component of the EEP consists of a positive-negative wave which begins soon after the electrical artifact generated by the stimulus. The positive peak of this wave (eP1) had an average positive peak latency of 8.39 ms and its negative trough (eN1) had an average latency of 16.32 ms, as shown in Table 2:

TABLE 2

Average latency (standard deviation in parentheses) of the vP1, vN1, vN2 and vP2 components of the VEP across the three cats. This has been compared to the average latency of the eP1, eN1, eN2, eP2 components of the EEP across the three cats. As would be expected the EEP has shorter latencies than the VEP, the latency difference between homologous components is shown in the table, along with the average latency shift across all components. Also shown is the average amplitude of the vP1-vN1 and vN2-vP2 waves.
LATENCY OF VEP AND EEP COMPONENTS

| VEP | Latency (ms) | EEP | Latency (ms) | Latency Shift (ms) |
|---|---|---|---|---|
| vP1 | 55.67 (5.38) | eP1 | 8.39 (0.28) | 47.28 |
| vN1 | 67.33 (7.81) | eN1 | 16.32 (1.77) | 51.01 |
| vN2 | 100.40 (17.67) | eN2 | 33.28 (5.56) | 67.12 |
| vP2 | 131.77 (27.47) | eP2 | 56.97 (2.94) | 74.79 |
| | | | Average Shift | 60.05 |

| Wave | VEP Amplitude (µV) |
|---|---|
| vP1-vN1 | 24.75 (15.47) |
| vN2-vP2 | 65.86 (33.10) |

Figure 21:
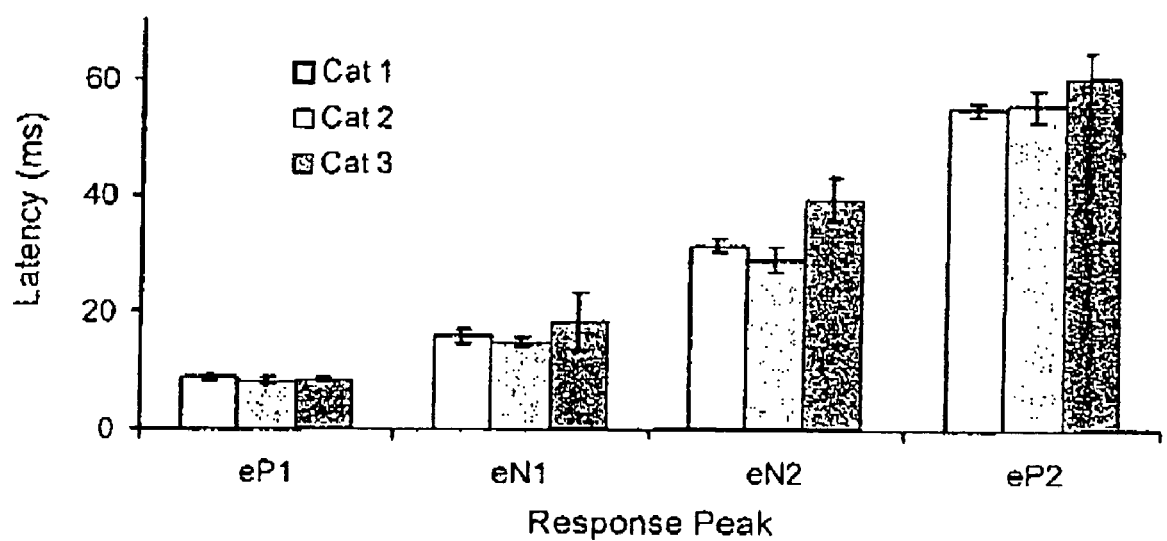
FIG. 21 is a graphical representation of latency of the eP1, eN1, eN2 and eP2 components of the EEP to extraocular retinal stimulation for the three cats. Error bars indicate +/−1 standard deviation.

The late component of the EEP was a negative-positive wave with the average latency of its negative trough (eN2) being 33.28 ms, and its positive peak being 56.97 ms. FIG. 21 compares the response latencies of the four EEP components to bipolar lateral-cathodal stimuli across the three cats. EEPs, as analysed by component latency, were consistent both within cats and between cats. However the relative amplitudes of the early or late components of the EEP were variable between cats.

The highest amplitude component of the VEP recorded to flash stimulation was a negative-positive wave (vN2-vP2) which occurred after 70 ms (Table 2). The VEP was compared with the EEP to extraocular retinal stimulation. The late wave of the EEP (eN2-eP2) had a smaller amplitude and a shorter latency as compared to the vN2-vP2 component of the VEP. This would be expected as electrical stimulation bypasses the time needed for photoreceptor processing by directly depolarizing the retinal neurons. The eN2 component of the EEP occurs 67.12 ms earlier than the vN2 component of the VEP. A smaller positive-negative wave vP1-vN1 was also identified in the VEP, which may be the VEP correlate of the eP1-eN1 wave of the EEP as it occurs at a similar latency shift to the eN2 and vN2 components of the EEP and VEP respectively.

Strength-Duration Curve for Extraocular Retinal Stimulation

The current intensity for eliciting a threshold (an early or late wave amplitude greater than twice the baseline noise level) EEP was measured for bipolar lateral-cathodal biphasic stimuli at phase durations between 20 µs and 1000 µs to determine strength-duration relationships in the three cats. These have been plotted in FIG. 22, along with the threshold charge-density curve averaged across all cats. Threshold decreased with increasing phase duration. The lowest current thresholds were obtained in Cat 1. It was possible to evoke visual cortex responses with stimuli of 500 µA when using 800 µs per phase pulses. The lowest charge-density threshold for an EEP was 8.92 µC/cm2, and was obtained in Cat 1 at a phase duration of 200 µs and a current intensity of 1.4 mA.

Cortical Response Amplitudes

Figure 23:
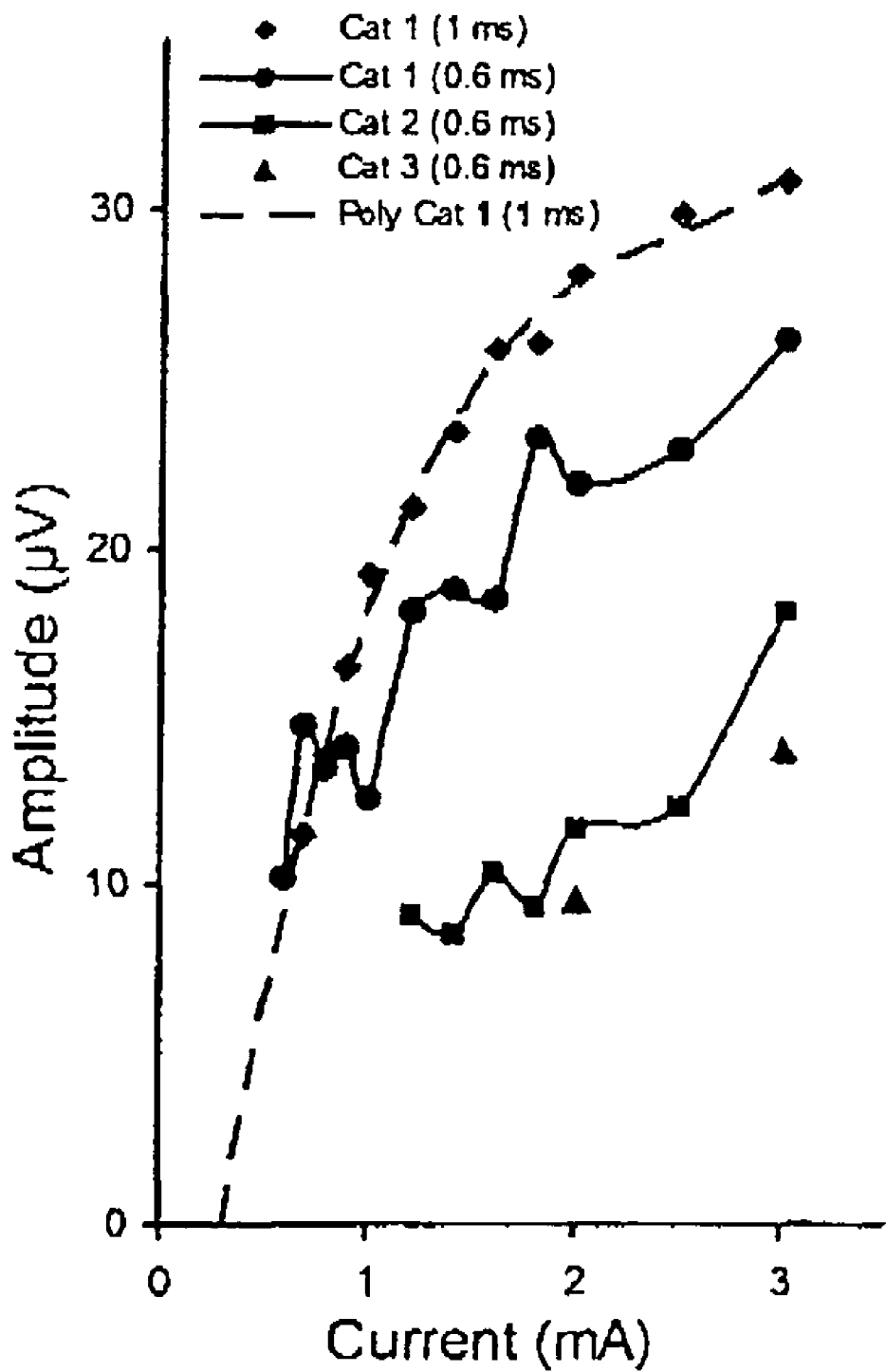
FIG. 23 is a graphical representation of EEP amplitude plotted as a function of current intensity in Cats 1, 2 and 3.

The amplitude of the eP1-eN1 wave of the EEP to bipolar lateral-cathodal stimuli was recorded in relation to changes in phase duration and current intensity levels in all cats. Stimuli of similar current level, but longer phase duration evoked higher amplitude EEPs (FIG. 23). Using stimuli at a constant phase duration, increases in the current intensity of the pulses evoked higher amplitude EEPs. In Cat 1, the increase in EEP amplitude started to plateau at current levels greater than 1.8 mA. EEP amplitudes were higher in Cat 1 compared to Cats 2 and 3 for stimuli at a similar phase duration. A third-order polynomial curve was fitted to the EEP responses from stimulus pulses with a 1000 µs phase duration obtained in Cat 1, and this was extrapolated to the x-axis (FIG. 23). This intersects the x-axis at a current level of 300 µA, which is the lowest threshold for an EEP that could be projected from the available data.

Electrode Configuration

Figure 24:
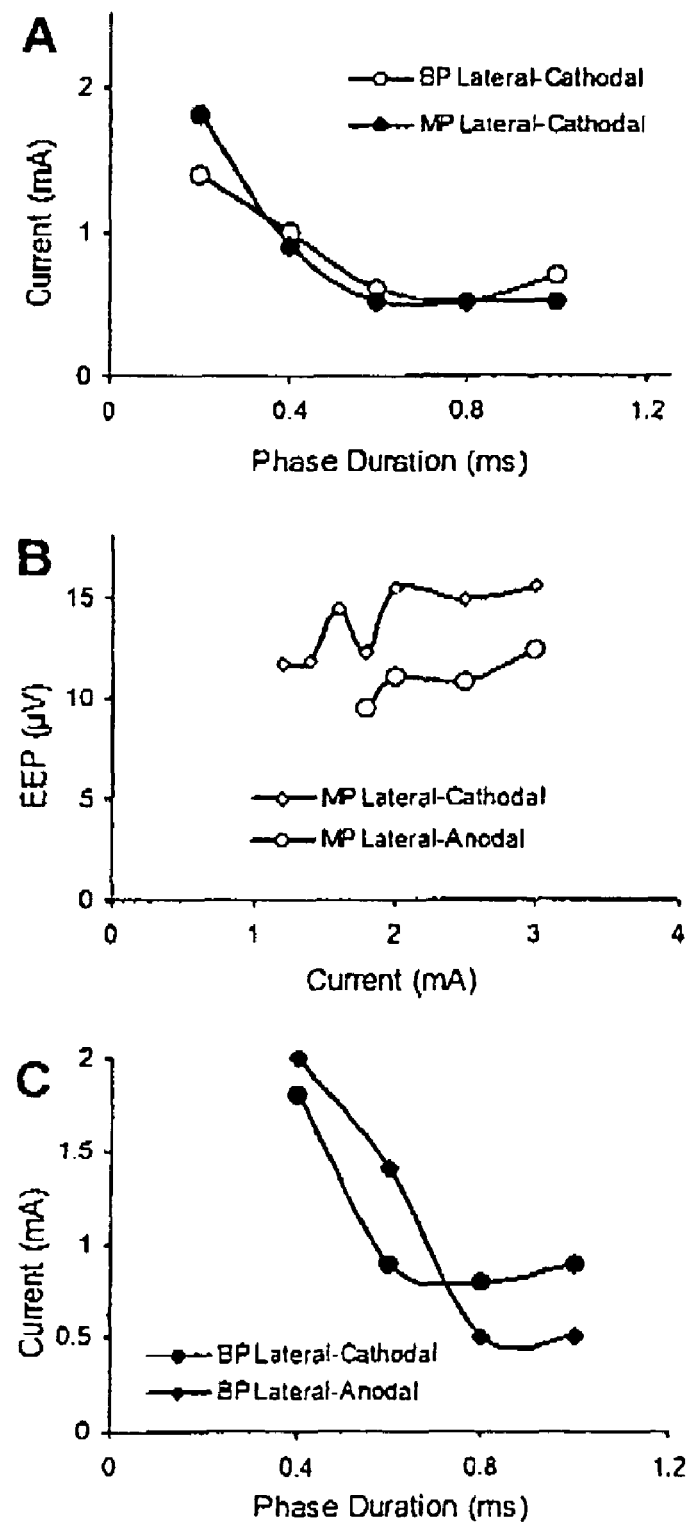
FIG. 24A is a graphical representation of a strength-duration curve for bipolar lateral cathodal stimulation in Cat 1.
FIG. 24B is a graphical representation of cathodal monopolar stimulation in Cat 2.
FIG. 24C is a graphical representation of bipolar stimulation with electrodes at alternate polarities in Cat 3.

Monopolar and bipolar stimuli, and the effects of polarity reversal were investigated by comparing strength-duration curves and EEP amplitudes. Bipolar lateral-cathodal stimulation was compared with monopolar lateral-cathodal stimuli. Both these stimulus configurations produced a similar profile of cortical response (FIG. 24A), reaching rheobase at a current level of 500 µA. Monopolar lateral-cathodal stimulation was compared with monopolar lateral-anodal stimulation. Cathodal extraocular monopolar stimulation consistently evoked higher amplitude EEPs than anodal stimulation (FIG. 24B). Bipolar lateral cathodal stimulation was compared with bipolar lateral anodal stimulation. These produced overlapping strength-duration curves, with lateral-anodal stimulation being more effective than lateral-cathodal stimulation at phase durations greater than 800 µs (FIG. 24C).

Discussion

Extraocular stimulation is a possible approach to developing a visual prosthesis to aid in the rehabilitation of blind patients. This study has demonstrated the feasibility of implanting electrodes on the sclera, and has evaluated their ability to evoke visual cortex responses from single pulse stimulation in the cat. The electrodes for this prototype prosthesis have been constructed from platinum and silicone, materials which have a good biocompatibility profile in human tissue. Access to the sclera can be gained through a simple surgical approach, and the extraocular electrode can be securely sutured or affixed by the shape of the extraocular device on the globe, its silicone base insulating the electrode from direct contact with overlying tissues or muscle. An extraocular device avoids the risks and complications associated with the more invasive surgery that would be needed for an epiretinal or subretinal implant, and avoids the placement of a foreign body intraocularly.

As larger electrodes are used for extraocular stimulation as compared with epiretinal implants, and the extraocular electrodes are further away from the target neurons in the retina, an extraocular device may not be able to match the potential resolution of a high-density intraocular implant, should such a device become a reality. However an extraocular device may be able to provide simple low resolution visual sensations to aid blind patients in their mobility and orientation. Due to the surgical and mechanical simplicity of an extraocular device, this may be a more clinically feasibly short-term goal than the restoration of more complex visual perception with intraocular implants.

A number of controls were performed to ensure that the responses were generated by localized electrical stimulation of the retina through the scleral electrodes, and were not the results of electrical artifact or stimulation through the cornea. Reversing the polarity of the stimulus did not invert the shape of the cortical response shown in FIG. 20. The EEP occurred at a shorter latency to the VEP, and at a similar latency shift to that shown in other studies. The amplitudes of the EEPs are significantly less than that of the VEP (FIG. 20), therefore only partial activation of the retina is occurring, favouring localised activation at the scleral electrode. Stimulation is occurring at the sclera and not through the cornea, as bipolar stimulation between two scleral electrodes evoked similar responses to monopolar stimulation using an ERG electrode as the return path (FIG. 24A). If stimulation was occurring through the cornea, bipolar stimulation would not evoke cortical responses, and the strength-duration curves for bipolar and monopolar stimulation would be very different.

Extraocular stimulation of the retina produces EEPs with early and late components. The EEP has a shorter latency than the VEP (Table 2) as would be expected if extraocular stimulation was bypassing the time required for photoreceptor processing by directly exciting neural cells in the retina. Due to the short latency of the EEP (FIG. 20), direct stimulation of the ganglion cells or their axons is probably occurring. The late (eN2-eP2) wave of the EEP occurs at a similar latency to the EEPs described by Dawson and Radtke in the cat (Dawson & Radtke, 1977, above), and Humayun and colleges in human studies (Humayun et al., 1996, above). However, the early wave (eP1-eN1) of the EEP recorded in this study with extraocular retinal stimulation has not been previously described. Due to its shorter latency, evaluation of this response may give a more direct indication of the effects of different stimulus parameters on retinal activation than the late wave of the EEP. The EEPs that were recorded exhibited the typical characteristics of a physiologic response. Alternating the polarity of the stimulus did not alternate the polarity of the recorded waveform. The EEP components had similar latencies within and between cats (FIG. 20), and when using different electrode configurations. Increasing the stimulus pulse width lowered the current threshold for a response, to produce typical strength-duration relationships. Also, the amplitude of the cortical evoked response saturated above certain current levels and did not show a linear increase (FIG. 23), which is more typical of a physiologic rather than artifactual response.

Figure 22:
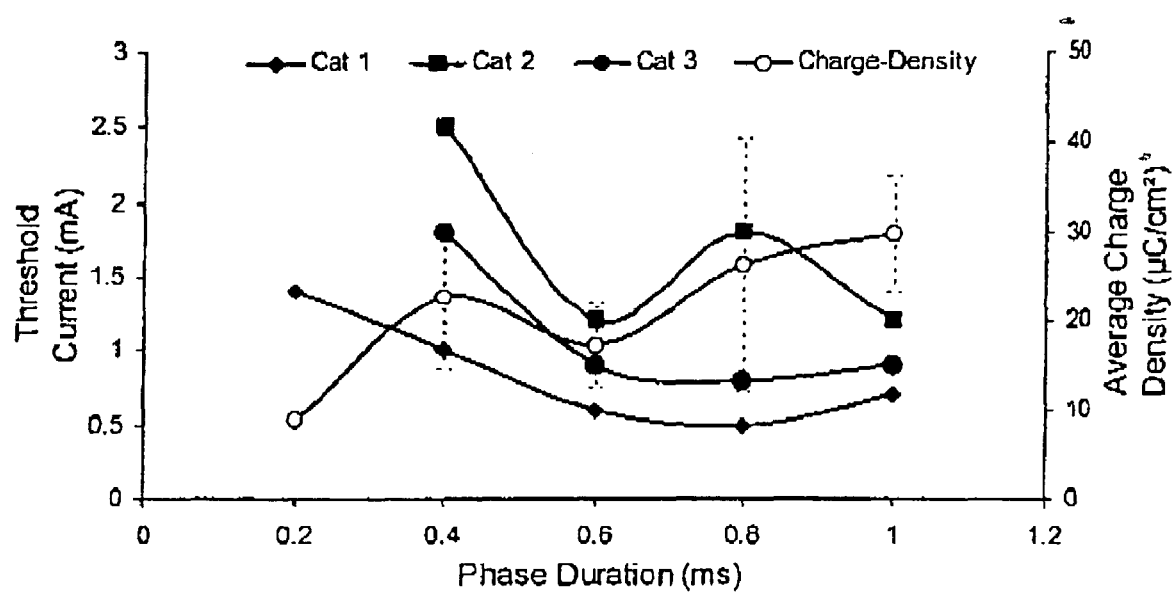
FIG. 22 is a graphical representation of threshold strength-duration curves for bipolar lateral-cathodal extraocular retinal stimulation.

Retinal activation was possible at current and charge-intensity levels that were well within safe limits for chronic neural stimulation with platinum electrodes. The threshold charge-density for evoking a cortical response in all cats, and across the range of phase durations investigated (FIG. 22) were well below charge injection limits for platinum electrodes of 100 µC/cm2 10, and within the safety limit of 52 µC/cm2 established for chronic human brain stimulation. We recorded thresholds as low as 500 µA with extraocular retinal stimulation (FIG. 22). When extrapolating from curves of EEP amplitude as a function of current intensity, thresholds as low as 300 µA were calculated (FIG. 23). The 2 mm diameter electrodes that were used in this study had a surface area of 0.0314 cm2, which is much larger than the electrode surface area in most epiretinal implants. We recorded threshold charge-densities as low as 8.92 µC/cm2 (FIG. 22). Studies in animals with photoreceptor degenerations are expected to display stimulus thresholds may be increased for diseased retinas.

A number of experiments were carried out to compare different electrode configurations for extraocular stimulation. Bipolar stimulation produced similar responses to monopolar stimulation (FIG. 24A). As would be expected, cathodal stimulation is more effective than anodal stimulation at exciting the neural tissue in the retina (FIG. 24B).

The large surface area of the sclera available posterior to the ora serrata will allow easy implantation of an array of at least about 20 electrodes of 1-2 mm diameter in extraocular devices.

LIST OF REFERENCES CITED

1. Sharma R K, & Ehinger B. Management of hereditary retinal degenerations: present status and future directions. *Survey of Ophthalmology* 1999; 43(5):427-44.
2. Chong N H & Bird A C. Management of inherited outer retinal dystrophies: present and future. *British Journal of Ophthalmology* 1999; 83(1):120-2.
3. Mitchell R N, & Cotran R S. Chapter 3: Repair: Cell Regeneration, Fibrosis, and Wound Healing. In: Kumar V, Cotran R S, Robbins S L, eds. Basic Pathology. 6 ed. Philadelphia: W. B. Saunders, 1997.
4. Scarlatis G. Optical prosthesis: visions of the future. *Jama* 2000; 283(17):2297.
5. Larkin M. Artificial-vision research comes into focus. *Lancet* 2000; 355(9209):1080.
6. Veraart, et al. Visual sensations produced by optic nerve stimulation using an implanted self-sizing spiral cuff electrode. *Brain Research* 1998; 813(1):181-6.
7. Maynard E M. Visual prostheses. *Annual Review of Biomedical Engineering* 2001; 3:145-68.
8. Brindley G S & Lewin W S. The sensations produced by electrical stimulation of the visual cortex. *Journal of Physiology* 1968; 196(2):479-93.
9. Humayun et al. Visual perception elicited by electrical stimulation of retina in blind humans. *Archives of Ophthalmology* 1996; 114(1):40-6.
10. Dobelle W H. Artificial vision for the blind by connecting a television camera to the visual cortex. *ASAIO Journal* 2000; 46(1):3-9.
11. Grumet et al. Multi-electrode stimulation and recording in the isolated retina. *Journal of Neuroscience Methods* 2000; 101(1):31-42.
12. Humayun M S. Intraocular retinal prosthesis. *Transactions of the American Ophthalmological Society* 2001; 99:271-300.
13. Humayun, et al. Pattern electrical stimulation of the human retina. *Vision Research* 1999; 39(15):2569-76.
14. Chow A Y, & Chow V Y. Subretinal electrical stimulation of the rabbit retina. *Neuroscience Letters* 1997; 225(1):13-6.
15. Stett, et al. Electrical multisite stimulation of the isolated chicken retina. *Vision Research* 2000; 40(13):1785-95.
16. Rizzo, et al. Retinal prosthesis: an encouraging first decade with major challenges ahead. *Ophthalmology* 2001; 108(1):13-4.
17. Margalit, et al. Retinal prosthesis for the blind. *Survey of Ophthalmology* 2002; 47(4):335-56.
18. Chow, et al. Subretinal Artificial Silicon Retina Microchip Implantation in Retinitis Pigmentosa Patients: Long Term Follow-Up. *ARVO Meeting Abstracts* 2003; 44(5):4205-.
19. Chapin & Moxon. Neural prostheses for restoration of sensory and motor function. Boca Raton: CRC Press, 2001.
20. Humayun et al. Visual perception in a blind subject with a chronic microelectronic retinal prosthesis. *Vision Res* 2003; 43(24):2573-81.
21. Dawson & Radtke. The electrical stimulation of the retina by indwelling electrodes. *Invest Ophthalmol Vis Sci* 1977; 16(3):249-52.
22. Yeomans J S. Principles of Brain Stimulation. New York: Oxford University Press, 1990.
23. Eckmiller R. Learning retina implants with epiretinal contacts. *Ophthalmic Research* 1997; 29(5):281-9.
24. Jensen et al. Thresholds for activation of rabbit retinal ganglion cells with an ultrafine, extracellular microelectrode. *Invest Ophthalmol Vis Sci* 2003; 44(8):3533-43.
25. Walter et al. Successful long-term implantation of electrically inactive epiretinal microelectrode arrays in rabbits. *Retina* 1999; 19(6):546-52.
26. Majji, et al. Longterm histological and electrophysiological results of an inactive epiretinal electrode array implantation in dogs. *Investigative Ophthalmology & Visual Science* 1999; 40(9):2073-81.
27. McCreery et al. Charge density and charge per phase as cofactors in neural injury induced by electrical stimulation. *IEEE Transactions on Biomedical Engineering* 1990; 37(10):996-1001.
28. Agnew & McCreery. Considerations for safety with chronically implanted nerve electrodes. *Epilepsia* 1990; 31(Suppl 2):S27-32.
29. Lamme et al. The role of primary visual cortex (V1) in visual awareness. *Vision Res* 2000; 40(10-12):1507-21.
30. Gordon et al. Parameters for direct cortical electrical stimulation in the human: histopathologic confirmation. *Electroencephalography & Clinical Neurophysiology* 1990; 75(5):371-7.
31. Jayakar P. Physiological principles of electrical stimulation. *Advances in Neurology* 1993; 63:17-27.
32. Tusa et al. The retinotopic organization of area 17 (striate cortex) in the cat. *J Comp Neurol* 1978; 177(2):213-35.

The invention claimed is:

1. An extraocular device for use as a visual prosthesis, the device comprising:
   an array of electrodes embedded in a base member, the base member shaped for placement on an outer scleral surface of an eye of a subject, permitting intimate physical contact between the array of electrodes and the outer scleral surface of the eye of the subject;
   a stimulator programmed to provide an electrical pulse to the array of electrodes and the outer scleral surface of the eye, to stimulate discrete local areas of retinal tissue in the eye and to generate discrete phosphenes in the eye of the subject, thus providing a neuroprosthetic effect and enabling the subject to perceive discrete spots of light; and
   a conducting means for electrically connecting the array of electrodes to the stimulator;
   wherein the electrical pulse does not travel to any electrode located on an internal side of the sclera of the subject.

2. The device according to claim 1, wherein the base member is retained on the scleral surface by sutures.

3. The device according to claim 1, further comprising a bioadhesive glue applied to the base member, wherein the base member is retained on the scleral surface by the bioadhesive glue.

4. The device according to claim 1, wherein the base member comprises two or more separate base members.

5. The device according to claim 4, wherein each base member is retained on the scleral surface by sutures.

6. The device according to claim 4, further comprising a bioadhesive glue applied to each base member, wherein each base member is retained on the scleral surface by the bioadhesive glue.

7. The device according to claim 1, wherein the base member is shaped to conform to the external scleral surface of the eye of a subject.

8. The device according to claim 7, wherein the shape of the base member retains it in a substantially fixed position on the scleral surface of the eye.

9. The device according to claim 1, wherein the base member includes perforations to decrease the degree of separation of connective tissues from the sclera of the eye.

10. The device according to claim 1, wherein the base member is a strip shape comprising a linear array of electrodes.

11. The device according to claim 1, wherein the base member is shaped to be placed on the scleral surface of the eye to fit around further anatomical structures of the eye.

12. The device according to claim 11, wherein the base member is shaped to fit around the attachment of one or more rectus muscles.

13. The device according to claim 12, wherein the base member completely surrounds the sclera of the eye.

14. The device according to claim 1, wherein the base member surrounds a portion of the sclera of the eye.

15. The device according to claim 1, wherein a posterior portion of the base member has an elongate aperture allowing sliding placement of the base member about the optic nerve of the eye.

16. The device according to claim 1, wherein the device has up to 1000 electrodes.

17. The device according to claim 16, wherein each electrode has an independent conducting means, each conducting means being insulated.

18. The device according to claim 1, wherein the stimulator is implanted in the body of the subject.

19. The device according to claim 18, wherein the stimulator is implanted inside the orbit of the subject.

20. The device according to claim 1, wherein the stimulator is located outside of the body, the conducting means exiting the body through a percutaneous connection to meet the stimulator.

21. The device according to claim 1, wherein the stimulator is powered by a battery.

22. The device according to claim 1, wherein the stimulator is powered and controlled by an inductive link from a transmission coil that has been placed outside the body.

23. The device according to claim 1, wherein the base member comprises a biocompatible material.

24. The device according to claim 23, wherein the biocompatible material is a silicone elastomer.

25. The device according to claim 1, wherein the conducting means is insulated with a biocompatible material.

26. The device according to claim 25, wherein the biocompatible material covers a connection between the conducting means and the stimulator.

27. The device according to claim 1, wherein the stimulator is controlled by a preprogrammed sequence of electrical stimulation.

28. The device according to claim 1, wherein electrodes of the array of electrodes comprise platinum or a platinum alloy.

29. The device according to claim 1, wherein the electrical impulse provided by the stimulator comprises a monopolar, bipolar or multi-polar electrical impulse.

30. The device according to claim 1, wherein the array of electrodes comprises three or more electrodes.

31. The device according to claim 1, wherein the array of electrodes comprises 21 platinum disc electrodes arranged in three rows.

32. The device according to claim 1, wherein the base member is shaped for placement on the outer scleral surface of the eye of the subject without disrupting attachment of the optic nerve.

33. The device according to claim 1, wherein the electrical pulse provided by the stimulator is a constant current biphasic pulse having a current intensity between about 1 µA and 10 µA, a frequency between about 0.01 Hz and 250 Hz, and a duration between about 10 µs and 10 ms.

34. An extraocular device for use as a visual prosthesis, the device comprising:
  an array of electrodes embedded in a base member, the base member shaped for placement on an outer scleral surface of an eye of a subject, permitting intimate physical contact between the array of electrodes and the outer scleral surface of the eye of the subject; and
  means for electrically stimulating the array of electrodes, thus providing an electrical pulse to the array of electrodes and the outer scleral surface of the eye of the subject, to stimulate discrete local areas of retinal tissue in the eye, thereby generating discrete phosphenes in the eye of the subject, thus providing a neuroprosthetic effect and enabling the subject to perceive discrete spots of light
  wherein the electrical pulse does not travel to any electrode located on an internal side of the sclera of the subject.

35. The device of claim 34, wherein the means for electrically stimulating the electrodes comprises a laser light source.

36. The device according to claim 34, wherein the electrical pulse provided by the means for electrically stimulating is a constant current biphasic pulse having a current intensity between about 1 µA and 10 µA, a frequency between about 0.01 Hz and 250 Hz, and a duration between about 10 µs and 10 ms.

37. A method of restoring or improving visual perception in a patient having a visual disorder, the method comprising
  applying an extraocular electrical pulse to an array of electrodes and an outer scleral surface of an eye of the patient, thereby stimulating discrete local areas of retinal tissue in the eye of the patient and generating discrete phosphenes in the eye of the patient, enabling the patient to perceive discrete spots of light;
  wherein the array of electrodes is embedded in a base member, the base member shaped for placement on an outer scleral surface of the eye of the patient permitting intimate physical contact between the array of electrodes and the outer scleral surface of the eye of the patient; and
  wherein the electrical pulse does not travel to any electrode located on an internal side of the sclera of the subject.

38. The method of claim 37, wherein the visual disorder is a retinal dystrophy selected from the group consisting of retinitis pigmentosa, Usher syndrome, age-related macular degeneration, Stargardt macular dystrophy, Leber congenital amaurosis or Bardet-Biedl syndrome.

39. The method according to claim 37, wherein applying the extraocular electrical pulse comprises providing is a constant current biphasic pulse having a current intensity between about 1 µA and 10 µA, a frequency between about 0.01 Hz and 250 Hz, and a duration between about 1 µs and 10 ms.

40. A method for generating phosphenes in a patient having a visual disorder, for a prosthetic effect, the method comprising applying an extraocular electrical impulse to an array of electrodes and an outer scleral surface of an eye of the patient, thereby stimulating discrete local areas of retinal cells of the eye of the patient and generating discrete phosphenes in the eye of the patient, thus providing a neuroprosthetic effect and enabling the patient to perceive discrete spots of light;

wherein the array of electrodes is embedded in a base member, the base member shaped for placement on the outer scleral surface of the eye of the patient permitting intimate physical contact between the array of electrodes and the outer scleral surface of the eye of the patient; and wherein the electrical impulse does not travel to any electrode located on an internal side of the sclera of the subject.

41. An extraocular neuroprosthesis, comprising:

a base member shaped for placement on an outer scleral surface of an eye of a subject, at a location corresponding to retinal tissue;

an array of electrodes disposed within the base member;

a conductor; and a stimulator, electrically connected to the array of electrodes via the conductor, which is programmed to provide an electric pulse through the conductor to the array of electrodes and, due to a location of the electrodes, to stimulate discrete local areas of retinal tissue, and to generate discrete phosphenes in the eye of the subject corresponding to one or more objects to be perceived by the subject.

42. A method of stimulating perception of discrete phosphenes by a subject, the method comprising:

providing an extraocular neuroprosthesis having an array of electrodes disposed in a base member;

disposing the base member on an outer scleral surface of an eye of the subject such that electrodes of the array of electrodes contact the outer scleral surface;

providing a constant current biphasic pulse to the array of electrodes, to stimulate discrete local areas of retinal tissue in the eye of the subject and produce phosphenes;

Wherein the biphasic pulse does not travel to any electrode located on an internal side of the sclera of the subject.

43. A method of stimulating prosthetic vision in a subject, the method comprising:

providing an electric pulse to an array of electrodes disposed in a base member on an outer scleral surface of an eye of the subject and generating discrete phosphenes corresponding to one or more objects to be perceived by the subject;

wherein the electrodes are disposed on a location on the outer scleral surface to enable stimulation of discrete local areas of retinal tissue, via the electric pulse, and wherein the electric pulse does not travel to any electrode located on an internal side of the sclera of the subject.

44. An extraocular device for use as a visual prosthesis, the device comprising:

an array of electrodes embedded in a base member, the array comprising at least one first electrode and at least one second electrode, the base member shaped for placement on an outer scleral surface of an eye of a subject, permitting intimate physical contact between the array of electrodes and the outer scleral surface of the eye of the subject;

a stimulator which provides an electric pulse from the at least one first electrode disposed on the outer scleral surface to the at least one second electrode disposed on the outer scleral surface, to stimulate discrete local areas of retinal tissue in the eye and to generate discrete phosphenes in the eye of the subject, thus providing a neuroprosthetic effect and enabling the subject to perceive discrete spots of light; and a conducting means for electrically connecting the array of electrodes to the stimulator.

45. An extraocular device for use as a visual prosthesis, the device comprising:

an array of electrodes comprising at least one first electrode embedded in a base member, the base member shaped for placement on an outer scleral surface of an eye of a subject, permitting intimate physical contact between the array of electrodes and the outer scleral surface of the eye of the subject;

at least one second electrode;

a stimulator which provides an electrical pulse from the at least one first electrode disposed on the outer scleral surface to the at least one second electrode disposed on the outer scleral surface, to stimulate discrete local areas of retinal tissue in the eye and to generate discrete phosphenes in they eye of the subject, thus providing a neuroprosthetic effect and enabling the subject to perceive discrete spots of light; and conducting means for electrically connecting the array of electrodes to the stimulator.

* * * * *